(12) United States Patent
Green et al.

(10) Patent No.: US 9,513,274 B2
(45) Date of Patent: Dec. 6, 2016

(54) DETERMINING ACID CONCENTRATION BY BOILING POINT

(71) Applicants: John Brian Green, Bartlesville, OK (US); Ricky Eugene Snelling, Tulsa, OK (US); Laura Lee Young, Bartlesville, OK (US); Dale Lee Embry, Houston, TX (US); Herbert Robert Pinnick, Jr., Bartlesville, OK (US)

(72) Inventors: John Brian Green, Bartlesville, OK (US); Ricky Eugene Snelling, Tulsa, OK (US); Laura Lee Young, Bartlesville, OK (US); Dale Lee Embry, Houston, TX (US); Herbert Robert Pinnick, Jr., Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 875 days.

(21) Appl. No.: 13/761,928

(22) Filed: Feb. 7, 2013

(65) Prior Publication Data
US 2013/0218481 A1 Aug. 22, 2013

Related U.S. Application Data

(60) Provisional application No. 61/600,368, filed on Feb. 17, 2012.

(51) Int. Cl.
| | | |
|---|---|---|
| *G01N 33/28* | (2006.01) | |
| *G01N 33/26* | (2006.01) | |
| *G01N 30/88* | (2006.01) | |
| *G01N 30/12* | (2006.01) | |
| *G01N 30/30* | (2006.01) | |

(52) U.S. Cl.
CPC .......... *G01N 33/2876* (2013.01); *G01N 30/88* (2013.01); *G01N 2030/126* (2013.01); *G01N 2030/3076* (2013.01); *G01N 2030/8854* (2013.01)

(58) Field of Classification Search
CPC  G01N 33/2876; G01N 33/2835; G01N 33/28; G01N 33/26; G01N 33/00; G01N 30/88; G01N 30/02; G01N 30/00
USPC ........................................ 702/30, 22; 436/57
See application file for complete search history.

(56) References Cited

U.S. PATENT DOCUMENTS

| | | | |
|---|---|---|---|
| 5,583,825 A | 12/1996 | Carrazzone et al. | |
| 6,121,411 A | 9/2000 | Sartori et al. | |
| 7,589,539 B2 | 9/2009 | Butler et al. | |
| 7,618,824 B2 | 11/2009 | Schaeffer et al. | |
| 8,118,994 B2 | 2/2012 | Messer et al. | |
| 2002/0086434 A1 | 7/2002 | Roussis et al. | |
| 2007/0026524 A1* | 2/2007 | Schaeffer ........... | G01N 33/2876 436/57 |
| 2007/0037288 A1* | 2/2007 | Qian .................. | G01N 33/2876 436/143 |
| 2008/0164137 A1 | 7/2008 | Messer et al. | |

FOREIGN PATENT DOCUMENTS

| | | |
|---|---|---|
| CN | 101023348 | 8/2007 |
| KR | 1020070059149 | 6/2007 |
| WO | 9607935 | 3/1996 |
| WO | 0248698 | 6/2002 |
| WO | 2007033253 | 3/2007 |

OTHER PUBLICATIONS

Sharma B. K., et al, Characterization of High-Boiling Petroleum Fractions using HPL and HTGC, Fuel Chemistry Division Preprints, 2002, 47(2), p. 640-642.*
Ryan P. Rodgers et al., "Petroleum Analysis", Analytical Chemistry, Anal, Chem, 2011, vol. 83, pp. 4670, left-hand column, line 1-p. 4671, left-hand column, last line, 2 pages.
Ryan P. Rodgers and Amy M. McKenna, "Petroleum Analysis", ACS Publications, Analytical Chemistry 2011, vol. 83, pp. 4665-4687.
I. Merdrignac and D. Espinat, "Physicochemical Characterization of Petroleum Fractions: the State of the Art", Oil & Gas Science and Technology, vol. 62, No. 1, Jan. 1, 2007, pp. 7-32.
Bhajendra N. Barman, Vincente L. Cebolla & Luis Membrado, "Chromatographic Techniques for Petroleum and Related Products", Critical Reviews in Analytic Chemical, vol. 30, Apr. 1, 2000, pp. 75-120.
Carey Bunks, Fatimetou M., Saleck, S., and G. Chavent, "Multiscale Seismic Waveform Inversion", Geophysics, vol. 60, No. 5, Sep.-Oct. 1995, pp. 1457-1473.
Kuangnan Qian, Kathleen E. Edwards, Gary J. Dechert, Stephen B. Jaffe, Larry A. Green and William N. Olmstead "Measurement of Total Acid Number (TAN) and TAN Boiling Point Distribution in Petroleum Products by Electrospray Ionization Mass Spectrometry", Feb. 2008 American Chemical Society, Analytical Chemistry, vol. 80, No. 3, pp. 849-855.

* cited by examiner

*Primary Examiner* — Christine T Mui
(74) *Attorney, Agent, or Firm* — Phillips 66 Company

(57) ABSTRACT

There is provided a method for determining Total Acid Number (TAN) in a fluid fossil fuel, such as a crude oil, comprising: separating said fluid fossil fuel by liquid chromatography into a plurality of fractions, comprising at least one acidic fraction; determining boiling point distribution of said crude oil, of said acidic fraction, and of said polyacidic fraction by simulated distillation (SD); and correlating said boiling point distributions to acid molecular weights to determine the TAN.

19 Claims, 20 Drawing Sheets

DETERMINING ACID CONCENTRATION BY BOILING POINT

CROSS-REFERENCE TO RELATED APPLICATIONS

This application is a non-provisional application which claims the benefit of and priority to U.S. Provisional Application Ser. No. 61/600,368 filed Feb. 17, 2012, entitled "Determining Acid Concentration by Boiling Point," which is hereby incorporated by reference in its entirety.

FIELD OF THE INVENTION

The invention relates to characterization of a hydrocarbon fuel, particularly to determining acid content in a fluid fossil fuel, such as crude oil or gas oil.

BACKGROUND OF THE INVENTION

Because of tightening market constraints, it is becoming more economically attractive to process higher acid crude oils. But along with the increased acidity comes problems in transportation and refinement of the crude oil due to higher metal corrosivity caused by the acid. Thus, it is necessary to develop a quick, accurate and inexpensive method for determining the acid content of a hydrocarbon fuel, particularly of crude oil.

A common measure of acid content in crude oil is Total Acid Number or "TAN." Predicting the TAN of a crude oil fraction is typically based on lab-scale distillation or pilot plant distillations. Unfortunately, these smaller-scale distillations have limited applicability to actual crude refining, because the sample is altered in the process of measurement. Heating a sample containing carboxylic or naphthenic acids leads to cracking, which lowers boiling point by reducing the average molecular weight of the fraction. Distillation temperatures also cause decarboxylation—that is, the loss of carboxylic acid functional groups—which lowers the acid number. The time and cost it takes to isolate the physical fractions also limits the usefulness of smaller-scale distillations.

Bachler et al. ("Simulated Distillation for Biofuel Analysis") describes simulated distillation for characterization of biodiesel, especially because carboxylic acid functionalities can interfere with analysis by physical distillation. In particular, Bachler reports that shorter chain fatty acids, as can be found in coconut oil, significantly change the distillation characteristics of the fuel.

Qian et al. ("Measurement of Total Acid Number (TAN) and TAN Boiling Point Distribution in Petroleum Products by Electrospray Ionization Mass Spectroscopy", *Anal. Chem.*, 2008, 80(3): 849-855) and US20070037288 describe a method to measure TAN and TAN boiling point based on negative ion electrospray ionization mass spectrometry (ESI-MS), using stearic acid as an internal standard. However, the method is limited to molecular weights of ≤650 g/mol ($C_{44}$) and requires specialized ESI-MS techniques and expensive equipment.

U.S. Pat. No. 7,618,824 describes a method for evaluating the acidity of an oil, wherein the acid functionality of the oil is isotopically enriched, for example with $^{13}C$, $^{18}O$ or $^{2}H$, and then measured using isotope ratio mass spectroscopy. Further specialized and expensive equipment is required to use this method.

US20020086434 describes a method for measuring acid distribution in a crude oil using chlorine negative ion chemical ionization mass spectrometry. The application does not teach or suggest separating fractions by chromatography, SDA, or correlation between paraffin boiling points and TAN. Also, specialized and expensive equipment is required for this method, thus reducing its cost effectiveness.

In the publications above, acidity of a crude was measured without distilling and titrating each distillation fraction, but ESI-MS and/or isotopic enrichment was needed to calculate TAN. What is lacking is a method for determining boiling point distribution of acids and for calculating TAN that does not expose the sample to time-consuming or harsh chemical conditions, but uses established processing techniques.

SUMMARY OF THE INVENTION

This invention allows direct determination of boiling point distribution for acids in a crude oil or gas oil with minimal thermal treatment, and without isotopic enrichment or mass spectrometry. Liquid fossil fuel is separated by liquid chromatography (LC) into at least four fractions based on polarity: non-acidic hydrocarbons; weakly acidic compounds, such as phenol; carboxylic acids; and polyacids containing two or more carboxylic acid groups. Simulated distillation (SD, or SimDist) determines the boiling point distributions of each chromatographic fraction, then, using a correlation between the boiling point ranges of paraffins, the boiling points of carboxylic acids, and the effective carbon numbers (ECN) for the acids are determined. The total acid number (TAN) of the crude is calculated based upon the acid concentration distribution in the crude as determined by this analysis.

Simulated Distillation is a GC technique for determining the boiling point distribution of a crude oil stock and details are available in various ASTM standards such as ASTM D 2887, ASTM D 3710, ASTM D 5307, ASTM D 6352, ASTM D 6417, ASTM D 7096 and ASTM D 7169.

For example, standard mixture of alkane compounds, usually up to $C_{44}$, is analyzed on a thin film, non-polar GC column. The resultant retention times for each alkane component are plotted against their known boiling point temperatures. Then the crude oil sample is weighed and spiked with a mixture of four compounds: $C_{14}$, $C_{15}$, $C_{16}$ and $C_{17}$. This sample is analyzed by the GC using the exact parameters employed in the standard run. A second sample is prepared like the first except without the internal standard spike, and also analyzed on the gas chromatograph. Software then analyzes the data to provide an estimate of boiling point distributions based on standard curves.

Paraffin boiling points and molecular weights are not easily correlated to acid boiling points and molecular weights, especially at the level of accuracy needed to calculate acid moles and TAN. Nonetheless, the inventors have produced a curve that can be used to predict TAN as a function of boiling point, improving resolution to a degree that could not be achieved with any conventional method (1 wt % increments). This invention allows the user to assess corrosivity of any distillation fraction without physical isolation of the hydrocarbon fraction, for example, at each tray in a distillation tower, and provides new insight into the details of the TAN curve and the acid profile of higher boiling residuals.

Specifically, this application provides a method for determining TAN in a fluid fossil fuel, comprising: separating said fluid fossil fuel by liquid chromatography into a plurality of fractions, comprising at least one acidic fraction; determining boiling point distribution of said fluid fossil fuel, of said acidic fraction, and of said polyacidic fraction by SD; and correlating said boiling point distributions to acid molecular weights to determine the TAN. The fluid fossil fuel can be a crude oil or a gas oil or residual oil.

The plurality of fractions can comprise a first fraction, a second fraction, a third fraction, and a fourth fraction. For example, the first fraction can be hydrocarbon, the second fraction weakly acidic compounds, the third fraction carboxylic acids, and the fourth fraction polyacids. The boiling point distribution can be determined for the crude oil, the third fraction and the fourth fraction. The TAN can have a resolution of at least 1 wt % and be calculated at each degree Fahrenheit.

In a particular embodiment, there is provided a method for determining TAN in a crude oil, comprising: separating said crude oil by liquid chromatography into a first fraction consisting essentially of hydrocarbons, a second fraction consisting essentially of weakly acidic compounds, a third fraction consisting essentially of carboxylic acids, and a fourth fraction consisting essentially of polyacids; determining boiling point distribution of said crude oil, of said third fraction, and of said fourth fraction by simulated distillation (SD); correlating the boiling point distributions to acid molecular weight using Equations 1-4:

$$\Delta T_{Acid} = 9.1 \left(\frac{T}{T_{100}}\right)^{-2.43}, \quad \text{(Equation 1)}$$

$$\Delta T_{Diacid} = 23.8 \left(\frac{T}{T_{100}}\right)^{-2.91}, \quad \text{(Equation 2)}$$

$$\Delta ECN_{Acid} = 4 + 2.2516 e^{-0.0838 CN}, \text{ and} \quad \text{(Equation 3)}$$

$$\Delta ECN_{Diacid} = 8 + 8.5671 e^{-0.0774 CN}, \quad \text{(Equation 4)}$$

wherein $\Delta T_{acid}$ and $\Delta T_{diacid}$ are corrections to be added to the reported n-paraffin boiling point to reflect the true boiling point of the mono-acids and the di-acids respectively; and wherein $\Delta ECN$ is the carbon number addition to the acid carbon number needed to have an n-paraffin with the same boiling point as the acid with carbon number CN; and calculating TAN based on said acid molecular weights. Distillation can occur up to an atmospheric equivalent boiling point of 720° C.

Acid fractions can be generated by preparative high performance liquid chromatography (HPLC) using a column packed with silica gel. The column can have an inner diameter of 1-5 cm, for example 2.5 cm, and can be 25-50 cm long, for example 30 cm long. The silica gel can be 60-Å silica gel. A ternary normal phase solvent gradient can be used, optionally containing an agent to basify the column, for example tetramethylammonium hydroxide (TMAH). The column is optionally temperature-controlled and equipped with an automatic fraction collector.

DESCRIPTION OF EMBODIMENTS OF THE INVENTION

Figure 1:
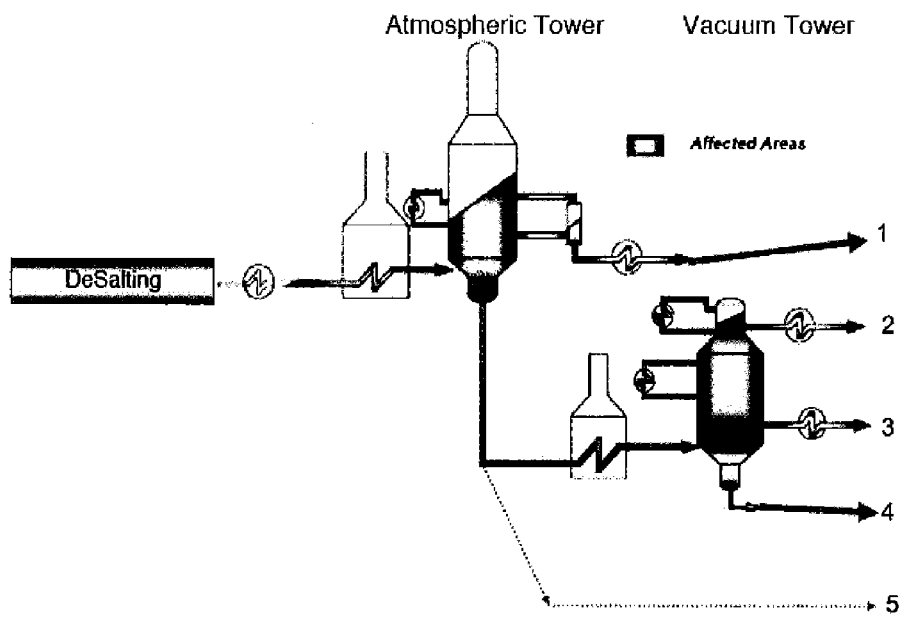
FIG. 1. A typical refinery process of distilling crude oil into motor fuel products and feed streams for other processes. The shaded areas illustrate where acid concentration in the hydrocarbons are a corrosion concern.

The following abbreviations are used herein:

| | |
|---|---|
| API | American Petroleum Institute |
| ASTM | American Society for Testing and Materials |
| CN | Carbon number |
| DI | Deionized |
| DIPPR | Design Institute for Physical Properties |
| ECN | Effective carbon number |
| EFC | Electronic flow control |
| ESI-MS | Electrospray ionization mass spectrometry |
| Est. | Estimated |
| FBP | Final boiling point |
| FID | Flame ionization detector |
| GC | Gas chromatography |
| GLC | Gas-liquid chromatography |
| HPLC | High performance liquid chromatography |
| IBP | Initial boiling point |
| KOH | Potassium hydroxide |
| LC | Liquid chromatography |
| MTBE | Methyl t-butyl ether |
| NAC | Naphthenic acid corrosion |
| NPLC | Normal phase liquid chromatography |
| RPLC | Reverse phase liquid chromatography |
| SD | Simulated distillation |
| SDA | Simulated distillation analysis |
| TAN | Total acid number |
| TMAH | Tetramethylammonium hydroxide |
| VGO | Vacuum gas oil |
| wt % | Weight percent |

"Fluid fossil fuel" refers to a type of fossil fuel that is in a substantially gaseous or liquid state at ambient conditions. The fluid fossil fuel can be a liquid with a relatively low viscosity, such as a light petroleum distillate, or with a relatively high viscosity, such bitumen. Examples of fluid fossil fuels include, but are not limited to, crude oil and gas oil.

"Crude oil" refers to a type of fossil fuel in the form of a mineral oil consisting of a mixture of hydrocarbons of natural origin, yellow to black in color, of variable specific gravity and viscosity. Crude oil is often referred to simply as "crude" or generally as "petroleum". Each crude oil has its own molecular characteristics and is typically named for its geography of origin, American Petroleum Institute (API) gravity, and sulfur content. Crude oil is "light" if it has low density or "heavy" if it has high density; "sweet" if it contains relatively little sulfur or "sour" if it contains substantial amounts of sulfur. Light crude oil is more desirable than heavy oil because it produces a higher yield of gasoline. Sweet crude oil commands a higher price than sour crude oil because it has fewer environmental problems and requires less refining to meet sulfur standards imposed on fuels in consuming countries.

"Total acid number" or "TAN" refers to a measure of the total acid content in a crude oil or a crude oil fraction obtained, for example, by distillation or by chromatography. Specifically, TAN can be expressed as the amount of potassium hydroxide (KOH) in milligrams needed to neutralize the acid in one gram of oil. TAN is used as a measure of corrosivity of an oil. Usually naphthenic acids in the crude oil cause corrosion problems, referred to as "naphthenic acid corrosion" or "NAC".

TAN can be deduced, for example, by potentiometric titration or by color indicator titration. In potentiometric titration, a sample is normally dissolved in toluene and propanol with trace water, and is titrated with alcoholic KOH. For TAN titrations, an electrode system is used that senses hydrogen ion activity. At the point when all the acid has been neutralized by the KOH, titration has been reached. In color indicating titration, a pH color indicator such as phenolphthalein is added to a sample, and KOH solution is titrated until the color permanently changes. TAN measurements can be made using a modified version of ASTM D 644.

"Chromatography" refers to a technique for separating a mixture, wherein the mixture is dissolved in a mobile phase and is passed through a stationary phase, separating components of the mixture based on differential partitioning between the mobile and stationary phases. Subtle differences in a compound's partition coefficient result in differential retention on the stationary phase, changing the separation. Chromatography can be preparative, analytical, or both. Preparative chromatography separates and purifies components of the mixture for further use. Analytical chromatography typically uses smaller amounts of material and is used to measure the relative proportions of components in a mixture.

"Liquid chromatography" or "LC" refers to a chromatographic technique in which the mobile phase is a liquid, and can be carried in a column or a plane. In column chromatography, the stationary phase is in a tube. The particles of the solid stationary phase or support can fill the tube's entire inside volume, as in a packed column, or can be concentrated on or along the inside tube wall, leaving an unrestricted path for the mobile phase, as in an open tubular column. In flash chromatography, solvent is driven through the column by applying positive pressure, allowing quicker and more efficient separation. In planar chromatography, the stationary phase is a plane, such as paper, or is on a plane, such a layer of solid particles adhered to a glass or metal plate (thin layer chromatography). Systems can also be linked with detectors and automatic fraction collectors. Gradient pumps for the mobile phase can provide quicker separations with less solvent usage.

In high performance liquid chromatography (HPLC), the sample is forced through a column packed with particles, a porous monolithic layer, or a porous membrane by a liquid at high pressure. Normal phase liquid chromatography (NPLC) uses a stationary phase that is more polar than the mobile phase, for example toluene as the mobile phase and silica as the stationary phase. Reverse phase liquid chromatography (RPLC) uses mobile and stationary phases of opposite polarities than NPLC, for example a water-methanol mixture as the mobile phase and a non-polar octadecylsilyl-terminated silica as the stationary phase.

Columns typically have an inner diameter of 2-5 cm, preferably 2.5 cm, and are 25-50 cm long, preferably 30 cm long. Larger diameter columns can accept larger sample injections but require faster flow rates to maintain an equivalent linear velocity, which is a function of the square of the column radius. Resolution can be lost in columns shorter than 30 cm. Columns longer than 30 cm provide greater resolution as function of the square root of length, but require more time per injection. Columns packed with silica having a particle size <10 µm require greater pump pressure to operate at equivalent flow rates. Particle sizes down to about 5-µm diameter are practical for prep scale HPLC. Sub-5-µm sizes can be expensive and are subject to excessive back pressure. Silica gel packings with pore sizes of 60 Å and particle sizes of about 10 µm are preferred.

Important elements include a silica column capable of handling injection volumes of 50 mL (20 g sample); at least a ternary solvent gradient based on toluene/methyl tert-butyl ether (MTBE)/methanol; a strongly basic mobile phase additive tetramethylammonium hydroxide (TMAH); instrumentation capable of generating ternary gradients utilizing a pump capable of delivering 30 mL/min flow at several hundred psi; and variable wavelength UV-visible detection coupled to an automated fraction collector. Solvent removal, fraction work-up and gravimetric determination of fraction yields are the final steps of the procedure.

"Gas chromatography" "gas-liquid chromatography", "GLC" or "GC" refers to a chromatographic technique in which the mobile phase is a gas. The stationary phase can be adhered to the inside of a small-diameter glass tube, for example a capillary, or is a solid matrix inside a larger metal tube, as in a packed column. The temperatures used in GC (>100° C.) make it unsuitable for high molecular weight biopolymers or proteins, but as an analytical technique, GC is well-suited for use in the petrochemical, environmental monitoring and remediation, and chemical fields.

"Simulated distillation", "SD", "simdis" or "SimDist" refers to an analytical, gas chromatographic (GC) technique for determining boiling point distribution of a fluid without physical distillation. SD is equivalent to a 100 theoretical plate physical distillation, is comparatively rapid, reproducible, and easily automated, requiring only microliter sample volumes and better defining initial boiling points (IBP) and final boiling points (FBP) than physical distillation. Sample runtimes can be about 30-60 minutes, with heating to maximum temperatures of about 450° C. and rapid cooling from 450° C. to 40° C. The boiling range distribution data obtained from SD can be used to evaluate new crude oils, confirm crude oil quality, monitor crude oil quality during transportation, optimize refinery processes or, as in the present application, to determine TAN.

The gas chromatograph used in SD can comprise a single channel, dual channel, or triple channel. The column must be non-polar. The injector can be temperature-controlled and on-column for capillary columns under electronic flow control (EFC). The column oven can be heated at a rate at least 2° C./s, for example 5° C./s, 10° C./s or 20° C./s, generating peak widths in the chromatogram of 50-200 ms. The oven can also be actively cooled to subambient temperatures. The GC detector is typically a flame ionization detector (FID). The SD analyzer optionally has an autosampler with a carousel heating and cooling plate for rapid sample throughput.

SD uses the accepted boiling point of n-parafins for calibration. ASTM D 7096 or D 7169 are preferred methodologies for this application, especially D 7169. ASTM D 7169 determines the boiling point distribution and cutpoint intervals of crude oils and residues by high temperature GC. ASTM D 7169 extends the applicability SD to samples that do not elute completely from the chromatographic system, and determines boiling point distribution up to an atmospheric equivalent of 720° C., corresponding to the elution of $n\text{-}C_{100}$. Accuracy is limited for the light end of the sample ($C_4$-$C_8$ compounds), as separation is typically incomplete in the presence of large amounts of solvent. A separate, higher resolution GC analysis of the light end portion of the sample may be necessary for a more accurate boiling point curve. ASTM D 7169 is generally not applicable, however, for materials containing a heterogeneous component, such as polyesters and polyolefins.

SD testing methods include those listed below in Table 1. For more information about standard test methods used in SD, visit the American Society for Testing and Materials (ASTM) International website (astm.org).

TABLE 1

Standard SimDist Test Methods

| Method (ASTM) | Carbon # range | | |
|---|---|---|---|
| D 7096 | | | gasoline |
| D 5399 | | | solvents |
| D 2887 | | | petroleum fractions |
| Ext. D 2887 | | | petroleum fractions |
| D 6352 | | | petroleum distillates |
| D 7169 | | | crude oil |
| DIN 51435 | | | petroleum fractions |
| IP 406-99 | | | petroleum fraction |
| IP 480 | | | middle distillates, Lubricating bas stocks |
| IP 507 | 7-125 | 100-775° C. | heavy distillate fuels and residuals |
| IP 545 | 1-125 | −150-775° C. | crude oil |

The present invention is exemplified with respect to determining total acid number in crude oil. However, this analysis is exemplary only, and the invention can be broadly applied to any hydrocarbon fuel, including biomass fuels. The following examples are intended to be illustrative only, and not unduly limit the scope of the appended claims.

Example 1

Correlation Between Boiling Points of N-Alkanes and N-Alkanoic Acids

Physical property databases were searched for the boiling points of n-alkanes and n-alkanoic acids. Acids larger than tridecanoic acid ($C_{13}$) were estimated as part of the Design Institute for Physical Properties (DIPPR®) projects at Brigham Young University (see dippr.byu.edu). The boiling points of the alkanoic acid were examined as a function of carbon number.

At identical retention times, the boiling points of the acids are related to the boiling points of the n-paraffins by the following correlations:

$$\Delta T_{Acid} = 9.1\left(\frac{T}{T_{100}}\right)^{-2.43} \quad \text{(Equation 1)}$$

$$\Delta T_{Diacid} = 23.8\left(\frac{T}{T_{100}}\right)^{-2.91} \quad \text{(Equation 2)}$$

where $\Delta T_{acid}$ and $\Delta T_{diacid}$ are corrections to be added to the reported n-paraffin boiling point to reflect the true boiling point of the mono-acids and the di-acids respectively.

A strong correlation (Equation 3) emerged between the carbon number of the alkanoic acid (carbon number, CN) and the carbon number of the n-alkane with the same boiling point as the acid (effective carbon number, ECN). Similarly, a strong correlation emerged for the CN dialkanoic acids and an n-alkane with the same boiling point as the diacid (Equation 4):

$$\Delta ECN_{Acid} = 4 + 2.2516 e^{-0.0838 CN} \quad \text{(Equation 3)}$$

$$\Delta ECN_{Diacid} = 8 + 8.5671 e^{0.0774 CN} \quad \text{(Equation 4)}$$

wherein $\Delta ECN$ is the carbon number addition to the acid carbon number needed to have an n-paraffin with the same boiling point as the acid with carbon number CN. These correlations have been used to fill in gaps in measured boiling points and to extrapolate the boiling point curves for these compounds to be consistent with the n-paraffin boiling points.

Table 2 below shows the relationship between carbon numbers for hydrocarbons and acids of different boiling points ranges, including acids with a single carboxylic acid group, or multiple acid groups.

TABLE 2

Relationship between carbon number of hydrocarbons (ECN) and acids (CN)

| Boiling Point Range (° F.) | Hydrocarbon Carbon Number (ECN) | Approximate Acid Carbon Number (CN) | Approximate Multiple Acid carbon number |
|---|---|---|---|
| 97-156 | $C_5$-$C_6$ | | |
| 345-385 | $C_{10}$-$C_{11}$ | acid $C_5$ | |
| 519-548 | $C_{15}$-$C_{16}$ | acid $C_{11}$ | |
| 601-626 | $C_{18}$-$C_{19}$ | acid $C_{14}$ | polyacid $C_5$ |
| 650-674 | $C_{20}$-$C_{21}$ | acid $C_{16}$ | polyacid $C_7$ |
| 755-774 | $C_{25}$-$C_{26}$ | acid $C_{21}$ | polyacid $C_{15}$ |
| 841-856 | $C_{30}$-$C_{31}$ | acid $C_{26}$ | polyacid $C_{21}$ |
| 972-982 | $C_{40}$-$C_{41}$ | acid $C_{36}$ | polyacid $C_{32}$ |
| 1067-1074 | $C_{50}$-$C_{51}$ | acid $C_{46}$ | polyacid $C_{42}$ |
| 1139-1146 | $C_{60}$-$C_{61}$ | acid $C_{56}$ | polyacid $C_{52}$ |
| 1197-1202 | $C_{70}$-$C_{71}$ | acid $C_{66}$ | polyacid $C_{62}$ |
| 1247-1252 | $C_{80}$-$C_{81}$ | acid $C_{76}$ | polyacid $C_{72}$ |
| 1292-1296 | $C_{90}$-$C_{91}$ | acid $C_{86}$ | polyacid $C_{82}$ |
| 1324-1328 | $C_{99}$-$C_{100}$ | acid $C_{96}$ | polyacid $C_{92}$ |

Example 2

Exemplary Distillation of a Crude Oil

Doba crude oil had an initial TAN of 4.8, an IBP of 97° F. and a FBP of 1328° F. as reported according to ASTM D 7169. Referring to FIG. 1, the crude oil was desalted, then distilled through an atmospheric tower followed by vacuum tower. The lowest boiling materials were taken off in the atmospheric tower; the higher boiling materials were taken off in the vacuum tower. Fraction 1 was taken from the atmospheric tower. The bottom fraction from the atmospheric tower was sent to the vacuum tower, producing Fractions 2-4: top, middle and bottom, respectively. Any residual material that could not be distilled became Fraction 5. See Table 3. The separation followed either ASTM D 2892 or ASTM D 5236.

TABLE 3

Fractions from Doba crude oil distillation

| Fraction | IBP (° F.) | FBP (° F.) | TAN | Crude weight % |
|---|---|---|---|---|
| 1 | 510 | 660 | 0.43 | 11.48 |
| 2 | 660 | 900 | 4.58 | 24.24 |
| 3 | 900 | 1050 | 10.15 | 14.08 |
| 4 | 1050 | 1328 | 2.77 | 26.92 |
| 5 | 660 | 1328 | 5.04 | 65.25 |

Example 3

General Method for Liquid Chromatography

Instead of physical distillation, liquid chromatography (LC) was used to separate a crude oil into fractions. LC avoided decomposition and decarboxylation caused by high distillation temperatures. These combined, chromatographic fractions were then analyzed for their boiling point distributions using simulated distillation.

Multigram fractions were enriched in nonacids (hydrocarbons and basic compounds; F1), weak acids (phenolic compounds and benzologs of pyrrole; F2), carboxylic acids (acyclic, naphthenic, and aromatic; F3), and multifunctional acids (more than one acidic group; F4) are generated. A final fraction (F5) could be generated by reversing the column flow at the end of a given series of replicate separations of a given sample. F5, also referred to as "backflush," consisted of compounds that did not elute from the column in the forward direction.

All samples were weighed, diluted and filtered through a tared 1-μm glass fiber filter before HPLC separation. Toluene, MTBE or their mixtures were used to dissolve samples and for filtering. The spent filter was dried and weighed and the net particulates (insolubles) counted in the overall material balance. The initial charge weight and weights of all fractions, including the backflush and filtered particulates, were recorded. Recovery of each fraction and total recovery (sum of all fractions) were reported.

The total sample size was at least 100 g. Because column loading capacity was limited to about 20 g of sample per injection, batches of sample were sequentially separated. Fractions from each batch were then combined to obtain sufficient quantities of weak acids, carboxylic acids and especially multifunctional acids for analysis. About 3-4 person-days were needed to prepare a 100-200-g petroleum sample. Most of the time was spent removing solvent, working up fractions, and obtaining constant weights of each fraction.

Minimally, the high performance liquid chromatograph (HPLC) needed multi-step ternary gradient capability, a 30 mL/min flow rate, 1000 psi pressure capability, column temperature control, variable wavelength UV detection, and automated fraction collection. For example, Waters (MILFORD™, MA) PREPLC™ had a 150 mL/min flow at 4000 psi, quaternary gradient capability, a model 2487 dual wavelength UV-visible detector, a TCM 2000 temperature control module (ANALYTICAL SALES AND SERVICES,™ Pompton Plains, N.J.) capable of temperature control to +/−0.1° C., RHEODYNE™ (Cotati, Calif.) model 7060 fraction collection, and backflush valves with pneumatic actuators. The fourth solvent channel of the quaternary solvent system was used to pump the sample onto the column at the start of each run, rather than manually loading a large volume injection loop (e.g., 80 mL). A 2 μm stainless steel filter was installed just in front of to the detector to prevent particulate entry into the detector flow cell.

The HPLC column had a 2.5 cm inner diameter, was 30 cm long, and was packed with 10 μm, 60 Å pore size silica gel. Solvent was removed by rotary evaporation at about 50° C., using high pressure air aspirators (AIR-VAC,™ Seymour, Conn.) to maintain vacuum near 500 mmHg. Solvents were high purity (FISHER OPTIMA™ or HPLC grades) and were prefiltered to ensure low particulate levels. TMAH was purchased as methanolic solution (20 and 25 wt % TMAH in methanol, ALDRICH,™ Milwaukee, Wis.).

BIOREX™ 70 ion exchange resin used to remove TMAH from the eluted product. It was of 100-200 mesh particle size, was the sodium (Na) form and was purchased from BIORAD™ (Hercules, Calif.). Used BIOREX™ 70 resin was converted to the sodium salt and then protonated. New resin comes as the sodium salt, so the sodium hydroxide wash was not needed for new resin. To treat, used BIOREX™ 70 resin was transferred to the large Buchner funnel using deionized (DI) water and treated with two 4 L bottles of 2M NaOH (320 g NaOH in 4 L DI water). The residual NaOH was rinsed out with 4-6 L DI water and the resin was then treated with 12 L of 2 M aqueous HCl (650 mL concentrated HCl in 4 L DI water). After HCl treatment, the resin was rinsed with DI water until pH paper indicated that the acid had been largely removed. The resin was treated with 12 L methanol, with part of the final bottle used to transfer the prepared resin to a suitable glass container for storage.

Figure 2:
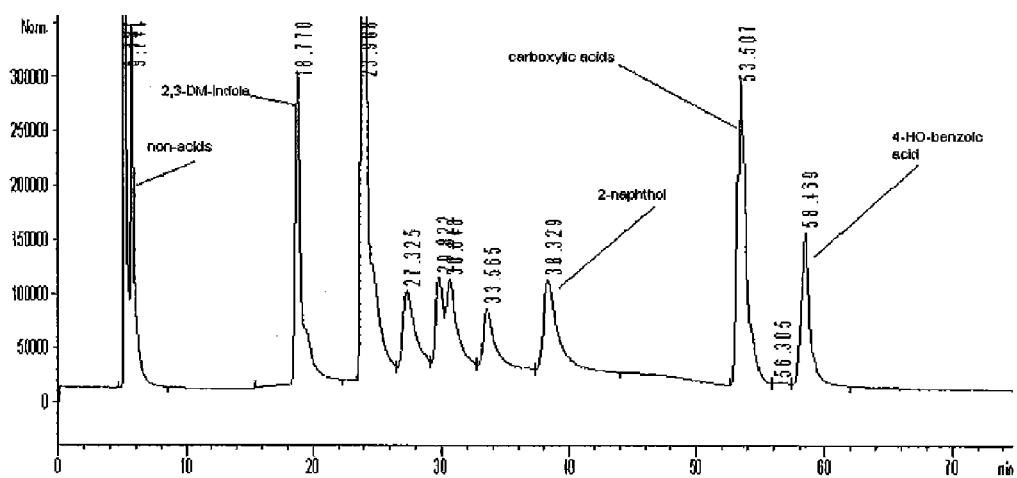
FIG. 2. HPLC chromatogram of an acid standard. Based on the retention times obtained from this chromatogram, the F1/F2, F2/F3, and F3/F4 cutpoints are set at 17, 40, and 56 minutes, respectively.

An acid standard was used to establish fraction collection times for preparative scale isolation of acidic compounds from crudes, distillates and resides. Table 4 lists the components of this acid standard in their order of elution. FIG. 2 shows the HPLC chromatogram for the acid standard. Based on the retention times obtained from this chromatogram, the F1/F2, F2/F3, and F3/F4 cutpoints were set at 17, 40, and 56 minutes, respectively.

TABLE 4

Composition of Acid Standard

| Compound Name | Approximate amount (g) | Notes |
|---|---|---|
| Dibenzofuran | 0.1 | Non-acid |
| Benzophenone | 0.4 | Non-acid |
| 2,3-Dimethylindole | 0.2 | Cut-point between F1 & F2 is 2 min before 2,3-dimethylindole retention time |
| Dibenzo[a,i]carbazole | 0.1 | Weak acid - should separate from those below |
| 2,4,5-Trimethylphenol | 0.3 | Weak acid - should separate from those below |
| o-Cresol | 0.3 | Weak acid - should separate from those below |
| 3,4-Dimethylphenol | 0.2 | Weak acid - should separate from those below |
| Phenol | 0.3 | Weak acid - should separate from those below |

TABLE 4-continued

Composition of Acid Standard

| Compound Name | Approximate amount (g) | Notes |
|---|---|---|
| 2-Naphthol | 0.3 | Cut-point between F2 & F3 is 1.5 min after 2-naphthol retention time |
| 1-Fluorenecarboxylic acid | 0.3 | Carboxylic acid |
| 2-Naphthoic acid | 0.2 | Cut-point between F3 & F4 is 2 min after 2-naphthoic acid retention time |
| 4-hydroxybenzoic acid | 0.2 | Di-acid; F4 runs out to 5 min after the time gradient re-equilibration is started-then fraction collector is switched to waste position. |
| methyl t-butyl ether (MTBE) | 80 mL | Solvent |
| Methanol | 20 mL | Solvent |

Elution conditions are listed in Table 5. As the column aged or if the retention times of the standard changed, elution conditions were adjusted accordingly.

TABLE 5

Solvent Gradient and Cut-points for HPLC Fractionation of Acids

| Time (min) | flow rate mL/min | Vol % Solvent A | B | C | D | Fraction collection valve setting/notes |
|---|---|---|---|---|---|---|
| 0 | 25 | — | — | — | 100 | Set to waste; column void volume is about 100 mL |
| 2 | 25 | — | — | — | 100 | Stop sample charge |
| 2.01 | 30 | 99 | 1 | — | — | — |
| 2.5 | 30 | 99 | 1 | — | — | Start F1 |
| 8 | 30 | 99 | 1 | — | — | Begin linear B ramp |
| 18 | 30 | — | — | — | — | Switch to F2 |
| 27 | 30 | 90 | 10 | — | — | Go to faster B ramp |
| 44 | 30 | 50 | 50 | — | — | Start linear C ramp |
| 45 | 30 | — | — | — | — | Switch to F3 |
| 61 | 30 | — | 80 | 20 | — | go to faster C ramp |
| 62.5 | 30 | — | — | — | — | Switch to F4 |
| 78 | 30 | — | 40 | 60 | — | — |
| 80 | 30 | 99 | 1 | — | — | Begin initial conditions |
| 85 | 30 | 99 | 1 | — | — | Switch to waste 1 |
| 86 | 30 | 99 | 1 | — | — | Advance to waste 2 |
| 89 | 30 | 99 | 1 | — | — | Re-equilibration complete |
| 90 | 0 | 99 | 1 | — | — | Stop flow |

Solvent A: 50:50 (v/v) toluene:MTBE
Solvent B: 70:30 (v/v) MTBE:MeOH with 3.00 mL 25% TMAH in methanol per 4 L
Solvent C: MeOH with 3.00 mL 20% TMAH in methanol per 4 L
Solvent D: filtered sample diluted in toluene
Column: 2.5 × 30 cm, 10 μm, 60 Å, Adsorbosil ™ silica
Column Temperature: 35° C.

The column was normally backflushed only after the entire sample had been separated. This step was necessary with all crudes and other samples containing non-distillable components. Backflushing consisted of initially eluting with 100% toluene; 90:10 toluene:Solvent C for 5 minutes; 50:50 toluene:Solvent C until the ultraviolet (UV) response drops to baseline; 100% Solvent B for 2 minutes, and finally 99:1 Solvent A:Solvent B for 10 minutes.

Figure 3:
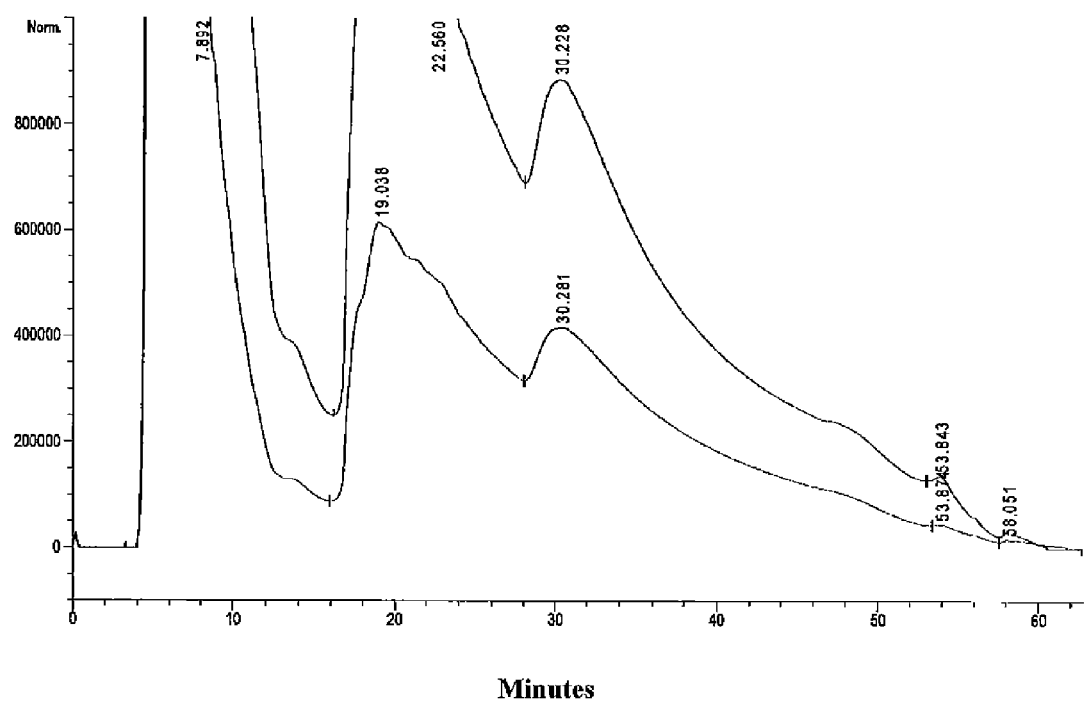
FIG. 3. HPLC chromatogram for Grane crude. Absorbances were detected at 280 nm (upper trace) and 350 nm (lower trace).
Figure 4:
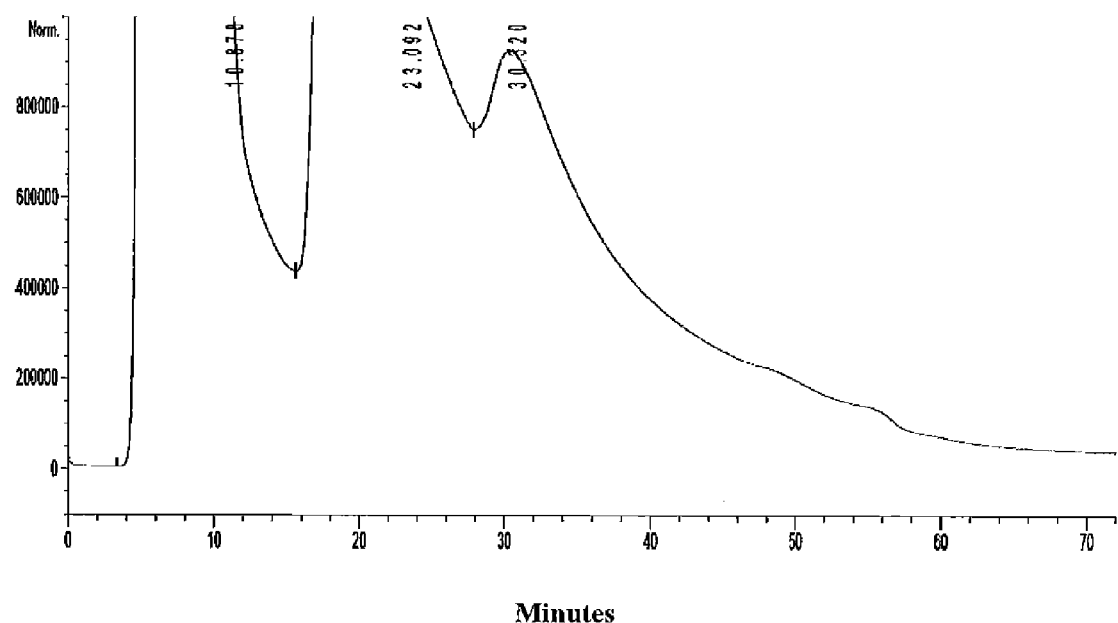
FIG. 4. HPLC chromatogram for San Joaquin Valley crude oil, indicating absorbances detected at 350 nm.

The dual wavelength detector was set at 290 nm and 350 nm. The 290 nm wavelength monitored the standard, and the less sensitive 350 nm was employed to monitor most samples. FIG. 3 shows HPLC chromatograms for Grane crude. Absorbances were detected at 280 nm (upper trace) and 350 nm (lower trace). FIG. 4 and HPLC chromatogram for San Joaquin Valley crude oil, indicating absorbances detected at 350 nm.

Example 4

Liquid Chromatography of Doba Crude Oil

A sample of Doba crude oil was separated into fractions by preparative HPLC following the general method described above in Example 3 above. A sample of 205.27 g of a crude oil separated into four factions: hydrocarbon (F1), weak acids (F2), carboxylic acids (F3), and polyacids (F4). Polyacids comprised primarily compounds with 2 or 3 carboxylic acid functional groups. Details for these fractions can be found at Table 6.

TABLE 6

Liquid chromatography of a Doba crude oil

| | F1 hydrocarbons | F2 weak acids | F3 carboxylic acids | F4 poly-acids |
|---|---|---|---|---|
| wt % of total sample | 92.91 | 7.53 | 3.63 | 0.80 |
| Est. wt % distillable acids | — | — | 3.40 | 0.00 |
| Est. wt % non-distillable acids | — | — | 0.23 | 0.80 |
| Est. distillable TAN | — | — | 3.34 | 0.00 |

The F3 fraction consistently contained the highest proportion of carboxylic acids of the fractions collected by weight. To see how the molecular weight distribution in F3 compared to that of the crude oil, SD was performed. Results can be seen in FIG. 5, wherein the vertical axis in the weight percent of the fraction and the horizontal axis is the effective carbon number (ECN) of that point. The carboxylic acid fraction F3 was separated from the crude oil using chromatography, which does not use boiling points for separation. Nonetheless, there was a significant difference in the boiling point distribution of F3 and that of the original material. The largest portion of crude oil has an ECN of $C_{13}$-$C_{26}$, whereas the largest portion of the carboxylic acid is higher boiling and has an ECN of $C_{30}$-$C_{40}$.

The acid isolation procedure provided a concentrate for detailed analysis/characterization of the acids from a given crude or distillate. The acid concentrate was substantially free of possible hydrocarbon interferences, allowing molecular characterization such as nuclear magnetic spectroscopy.

Example 5

Simulated Distillation Compared to Actual Distillation

TAN-SimDist provided several advantages. The resolution was improved over conventional TAN assay methods. TAN patterns were visualized in crude oils with small weight percent increments that would be expensive to produce by conventional methods. TAN-SimDist also provided new information about the TAN profile for the 1000-1350° F. range materials. Distillable boiling point profile of diacids in crudes was new information provided by this procedure. The weight percent fraction of polyacids was small; however, for some samples this fraction was a substantial portion of the TAN value for the high boiling fractions. Predicting diacid content was valuable because diacids may be more corrosive than monoacids.

Six crude oils Petrozuata Bitumen, Bohai Bay, Doba, Grane, Heidrun, and San Joaquin Valley Heavy and their gas oils were analyzed. The samples were weighed from (0.2-0.25 g) to the nearest 0.1 mg and 10 mL of $CS_2$ was added. Prepared solutions were stored at 4° C. Samples that are solid or semi-solid at room temperature required heating up 60° C. to pour them into a weighed container.

Simulated distillation was performed using D 7169-05, as described by "Designation D 7169-05: Standard Test Method for Boiling Point Distribution of Samples with Residues Such as Crude Oils and Atmospheric and Vacuum Residues by High Temperature Gas Chromatography", ASTM International, 2005, incorporated herein by reference in its entirety. The SimDist Expert 9.4 software application evaluated raw data to produce simulated distillation tables.

D 7169-05 used a GC with an inlet, capillary column under temperature control, an FID, and a data acquisition system that operated in slice mode. Retention time calibration mixture was used to develop a retention time versus boiling point curve. Reference Oil 5010 fully eluted from the column under the conditions of the test method and whose boiling point distribution had been characterized in Test Method D 6352 was used to determine the detector response factor. Solvent injections were made and the resulting signal was subtracted from both the response factor standard and the sample chromatogram. Finally, the sample solution was injected and, using the response factor, the amount of recovered sample was calculated. After converting the retention times of the sample slices to temperature, the boiling point distribution was calculated up to the recovered amount.

The gas chromatograph had a cryogenic valve to cool the oven to subambient temperatures. The HD maintained a temperature 5-10° C. higher than the highest column temperature, possessing a jet orifice of about 0.018 inch (0.45 mm) to delay the plugging from column bleed, a sensitivity of 0.005 coulombs/g and a linear range of $10.^6$ The inlet operated in a temperature-programmed mode from 50° C. to the final temperature of the oven, and the inlet's temperature, at any time during the analysis, was equal to or greater than the oven temperature. Gas purifiers removed traces of oxygen, moisture and other impurities, such as hydrocarbons, present in the carrier gas.

The data system acquired data at rate of at least 10 Hz, corresponding to slices of 0.1 second, which was necessary to obtain a minimum number of slices void of sample or solvent elution immediately after injection. Optionally, an integrator digitized the signal and acquired chromatograms of the retention time calibration mixture, sample, solvent, and reference oil standard. The auto sampler reproducibly injected small sample volumes (0.1 to 0.2 μL). Constant flow conditions were used, with the flow rate at the beginning of the oven temperature program not differing more than 1% from the flow measured at the final oven temperature.

The bonded polydimethylsiloxane column had an inner diameter of 0.5 mm and a film thickness of 0.09-0.17 μm. The column sustained temperatures of 435° C. under temperature programming. The column eluted $C_{100}$ at its highest temperature. Column resolution was between 1.8 and 4.0, as determined from the separation of $C_{50}$ and $C_{52}$ in the retention time calibration mixture chromatogram.

Figure 6:
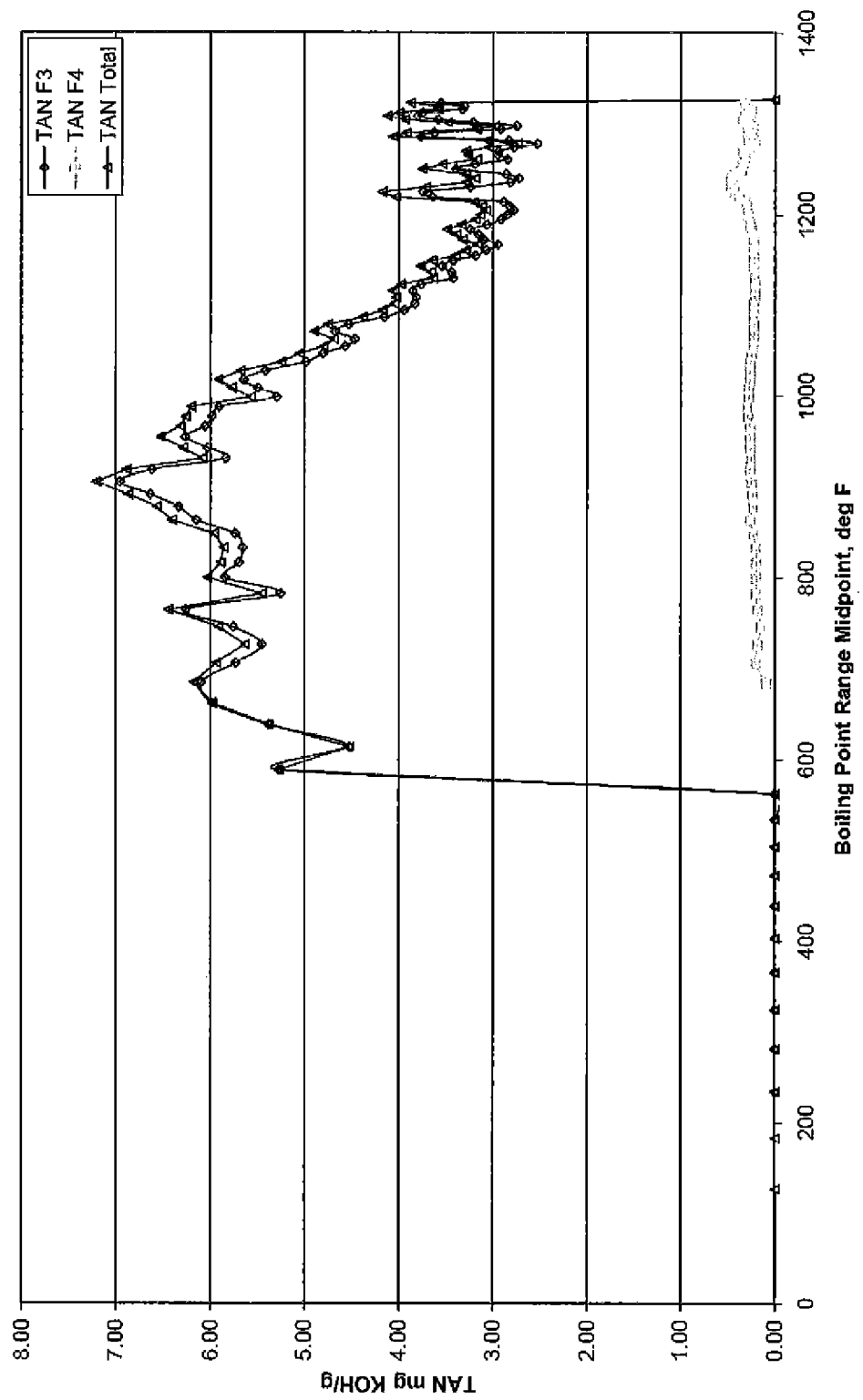
FIG. 6. SD results for Petrozuata Bitumen crude oil.
Figure 7:
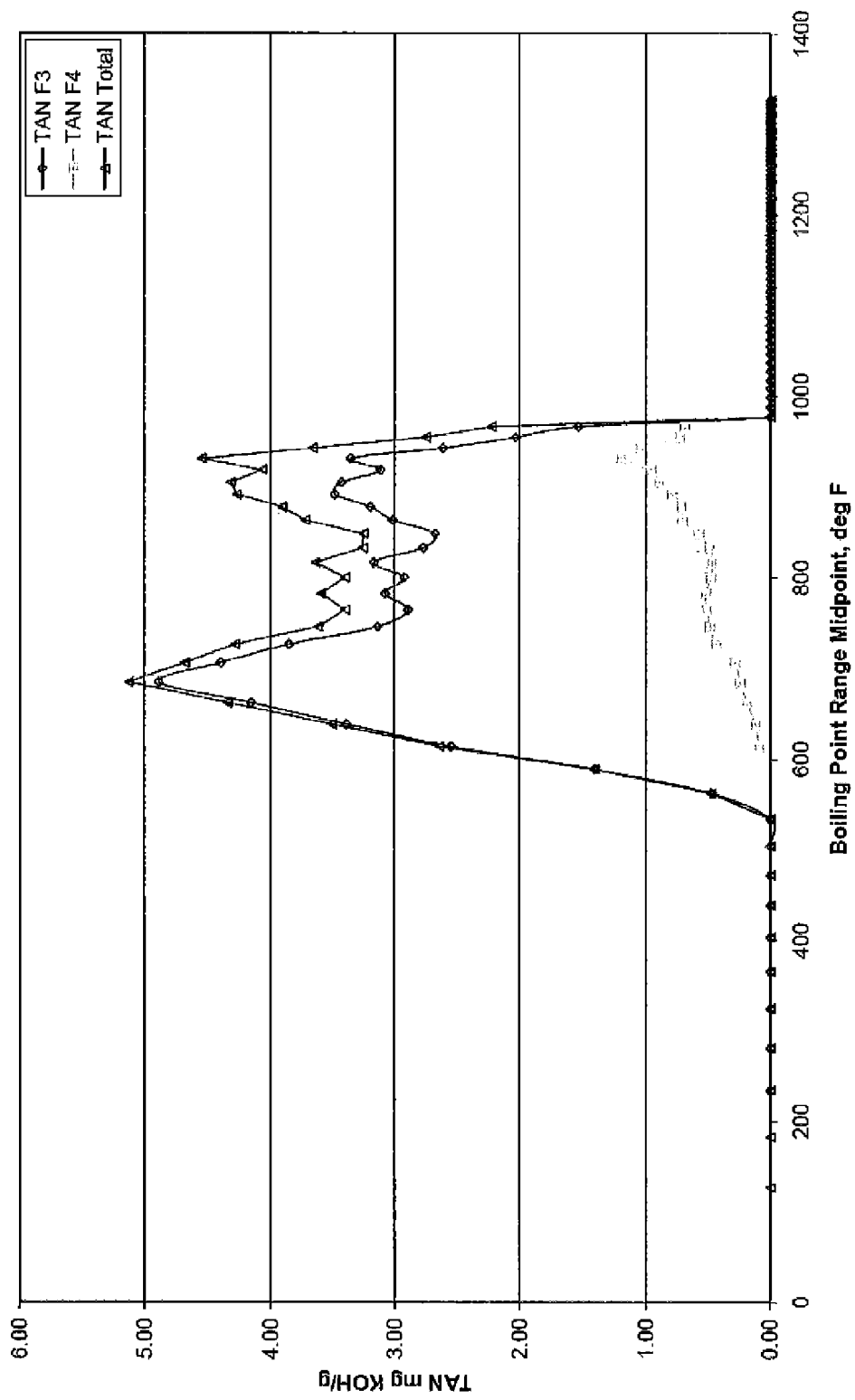
FIG. 7. SD results for Petrozuata Bitumen gas oil.
Figure 8:
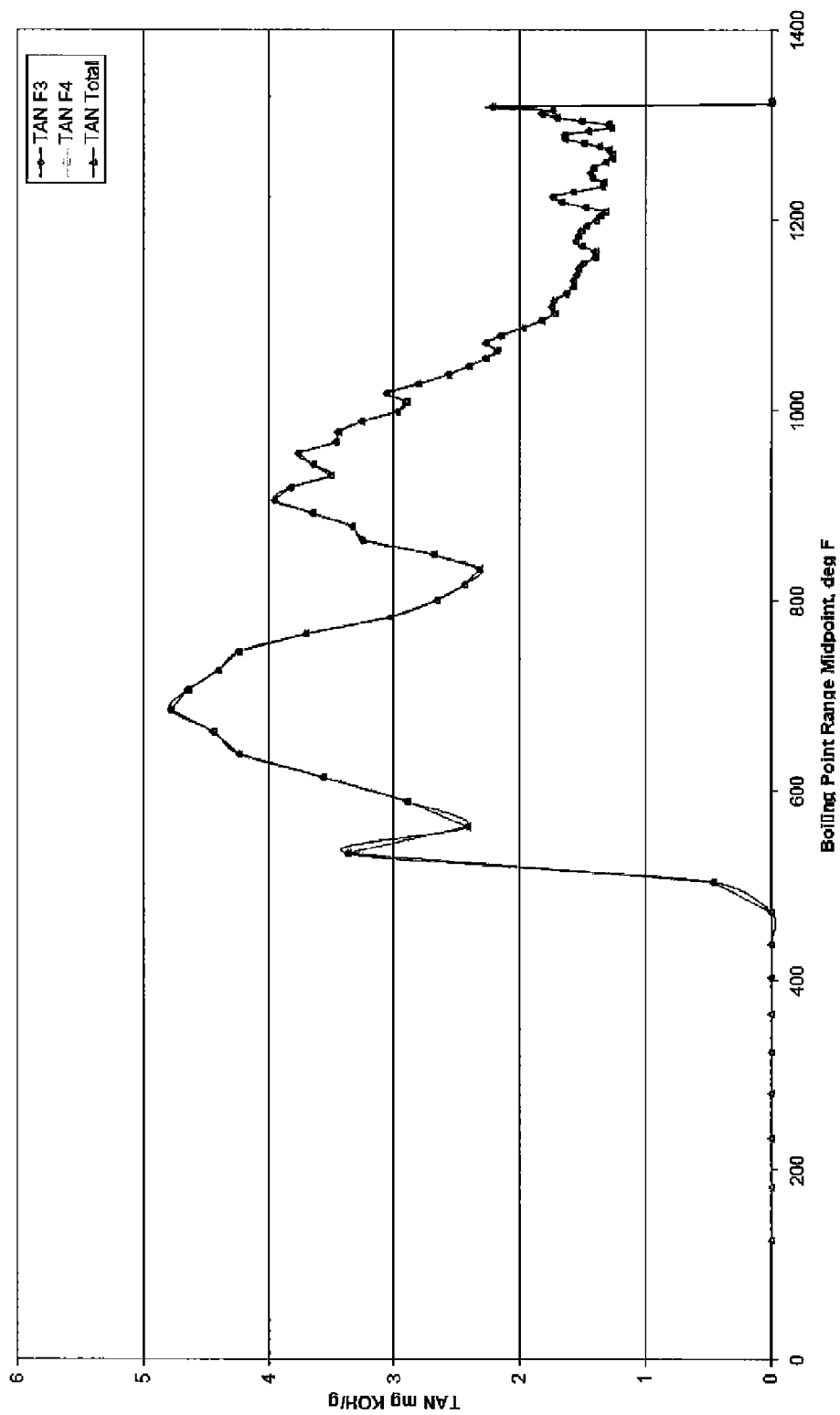
FIG. 8. SD results for Bohai Bay crude oil.
Figure 9:
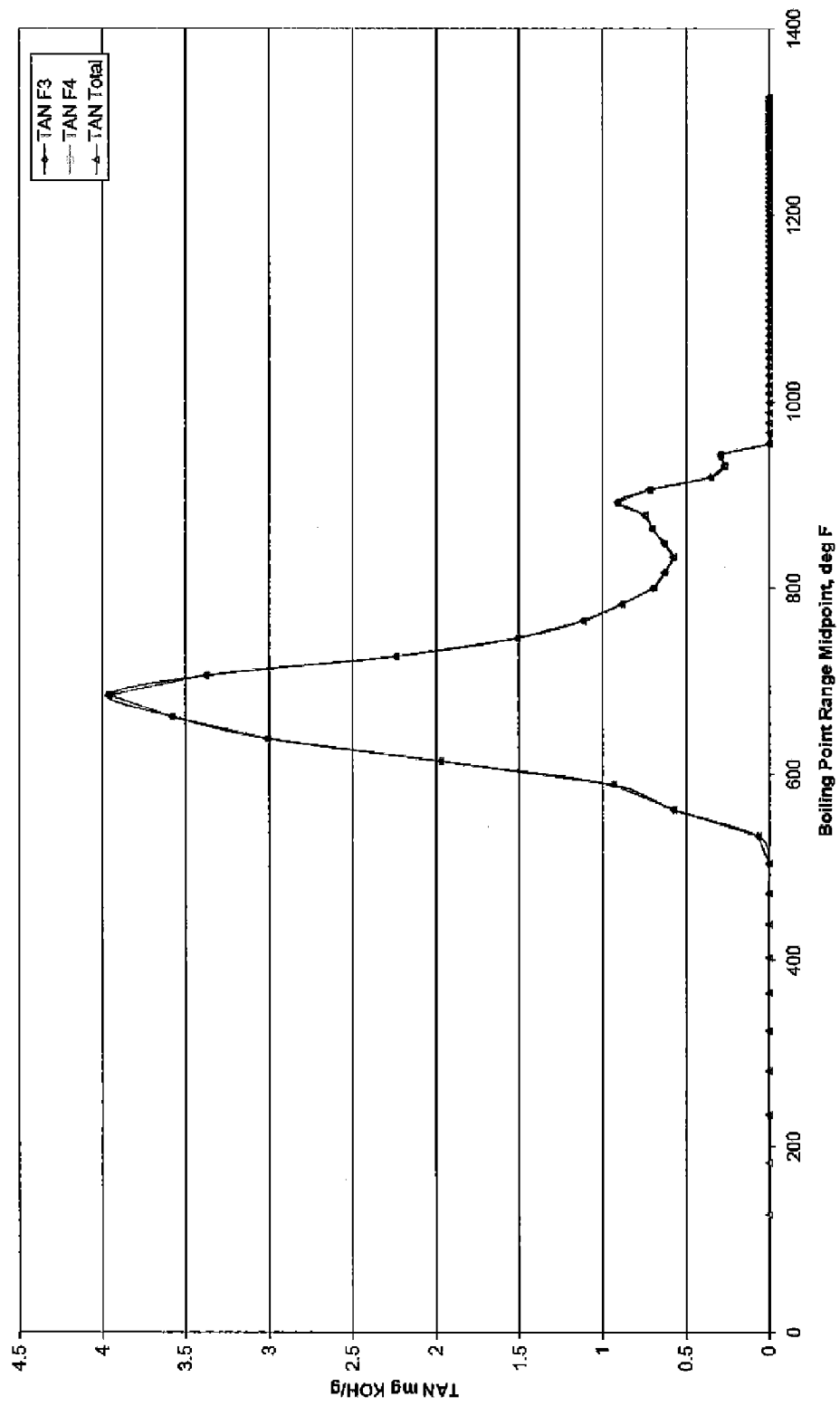
FIG. 9. SD results for Bohai Bay gas oil.
Figure 11:
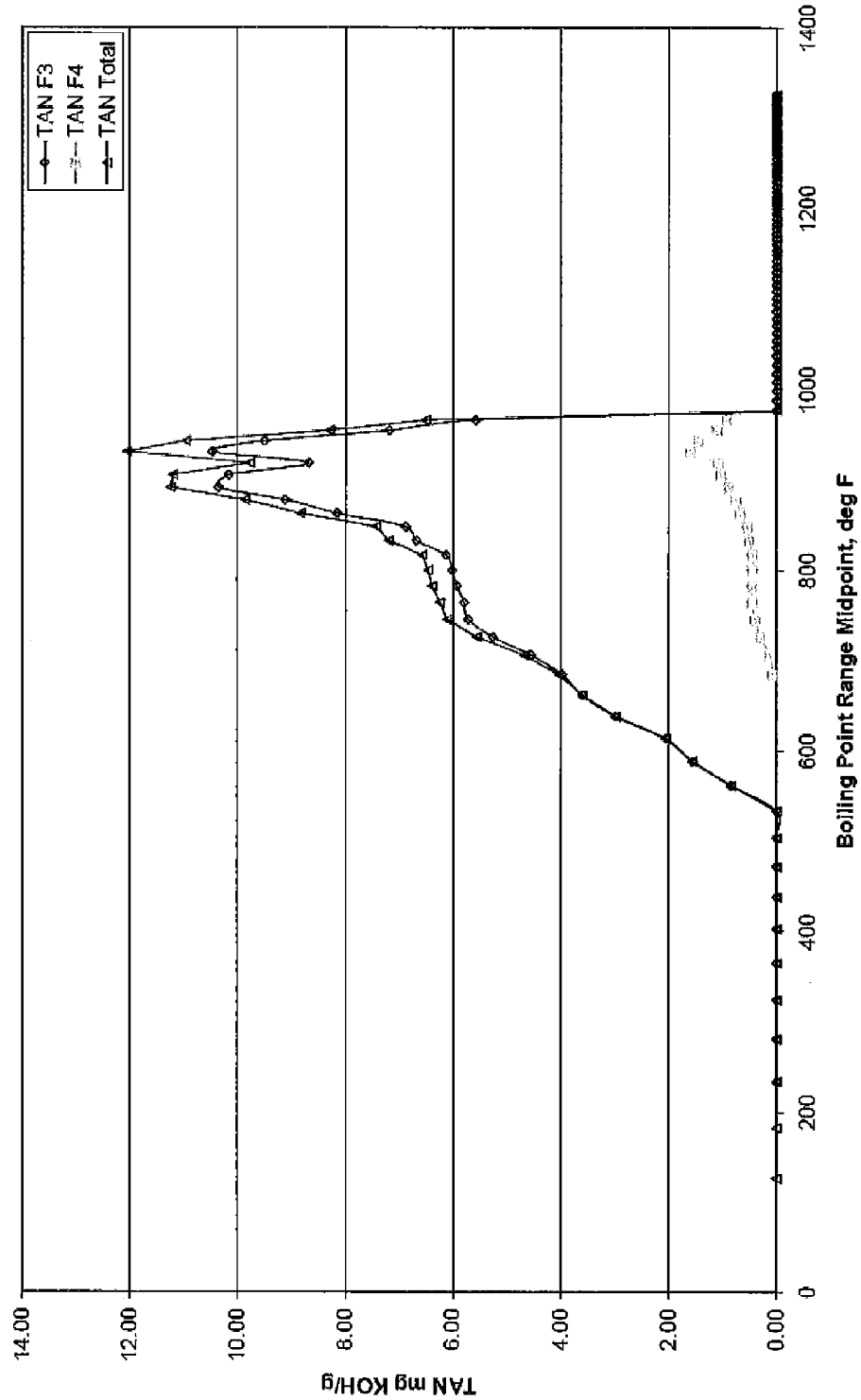
FIG. 11. SD results for Doha gas oil.
Figures 12, 13:
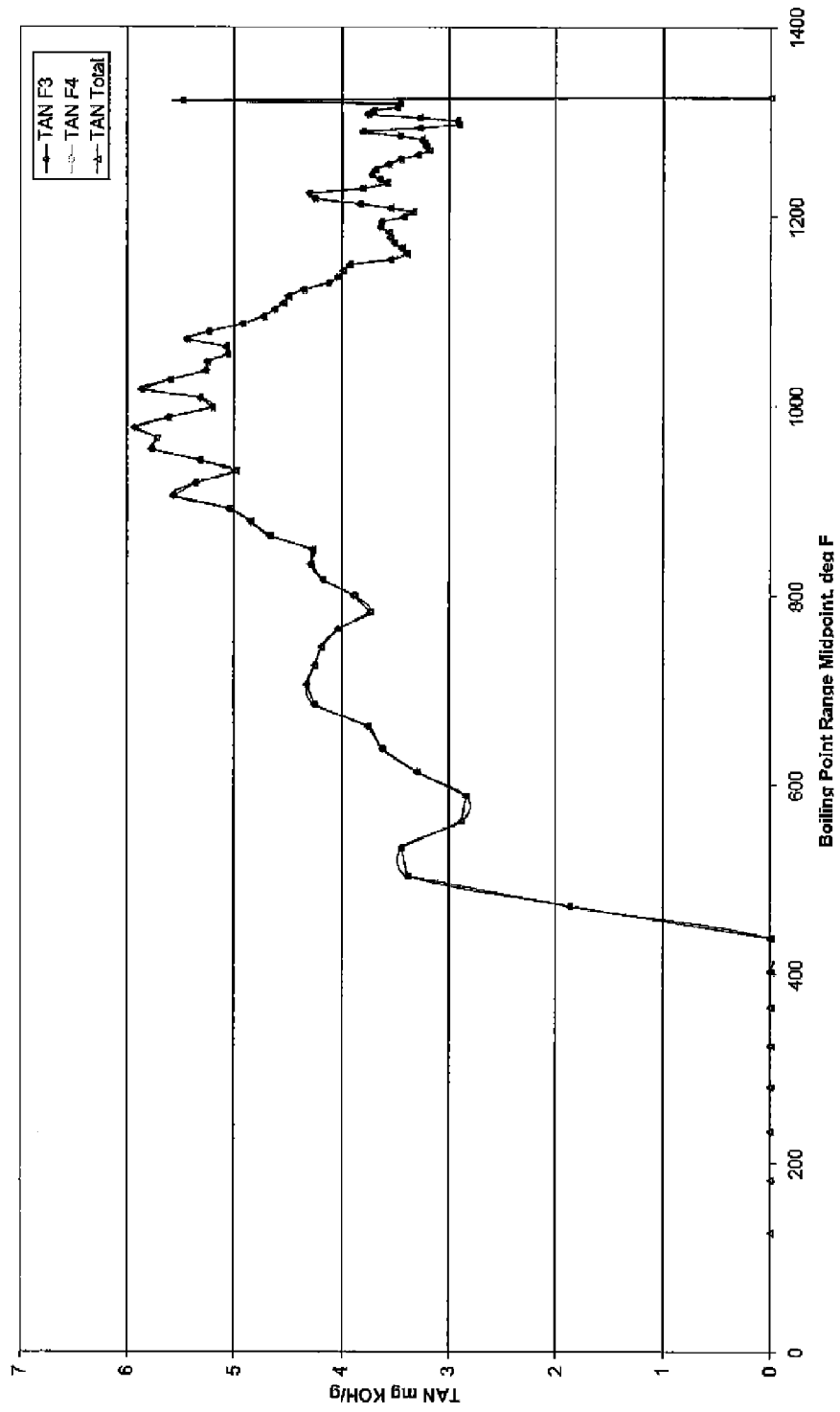
FIG. 12. SD results for Grane crude oil.
FIG. 13. SD results for Grane gas oil.
Figure 13:
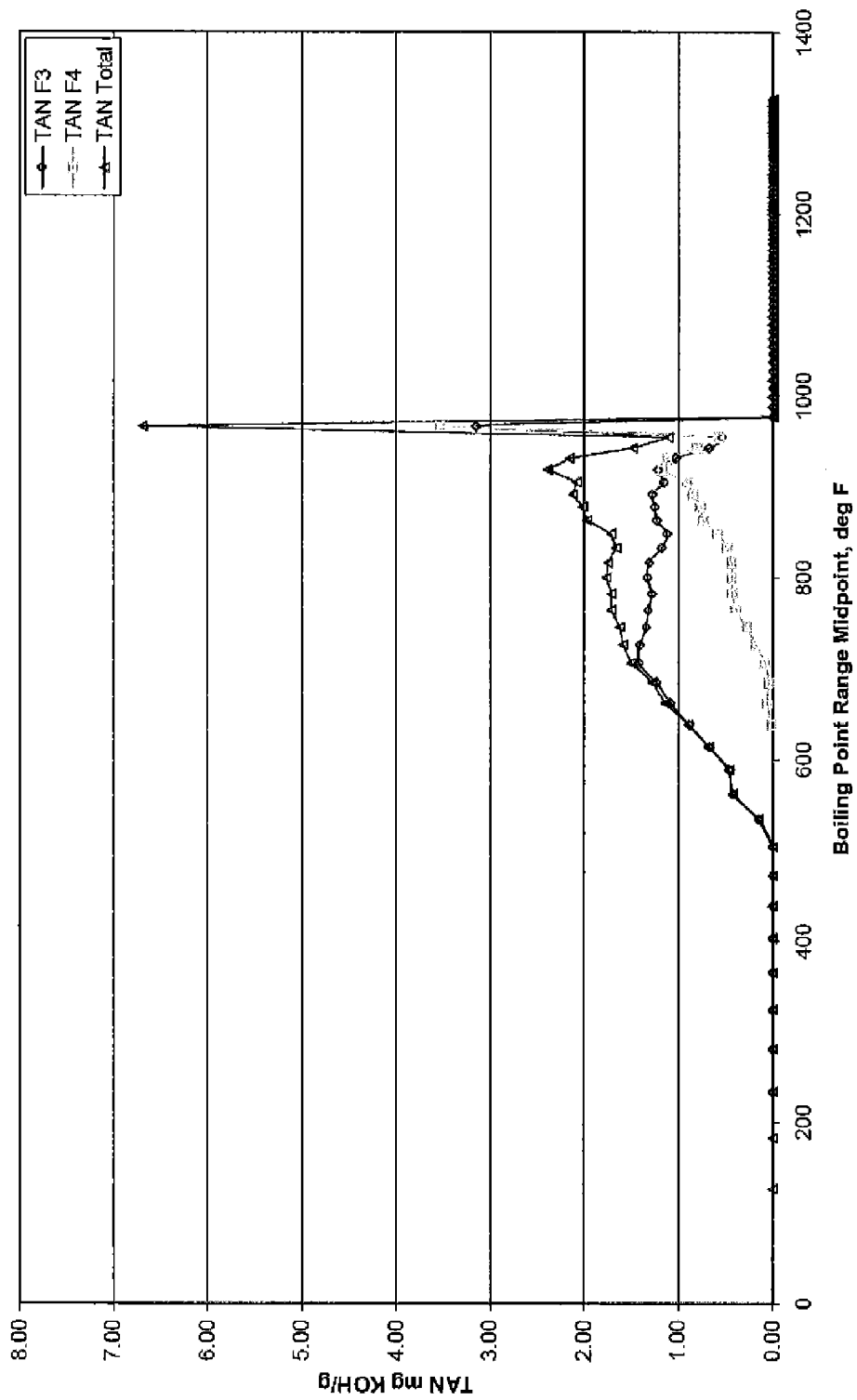
Figure 14:
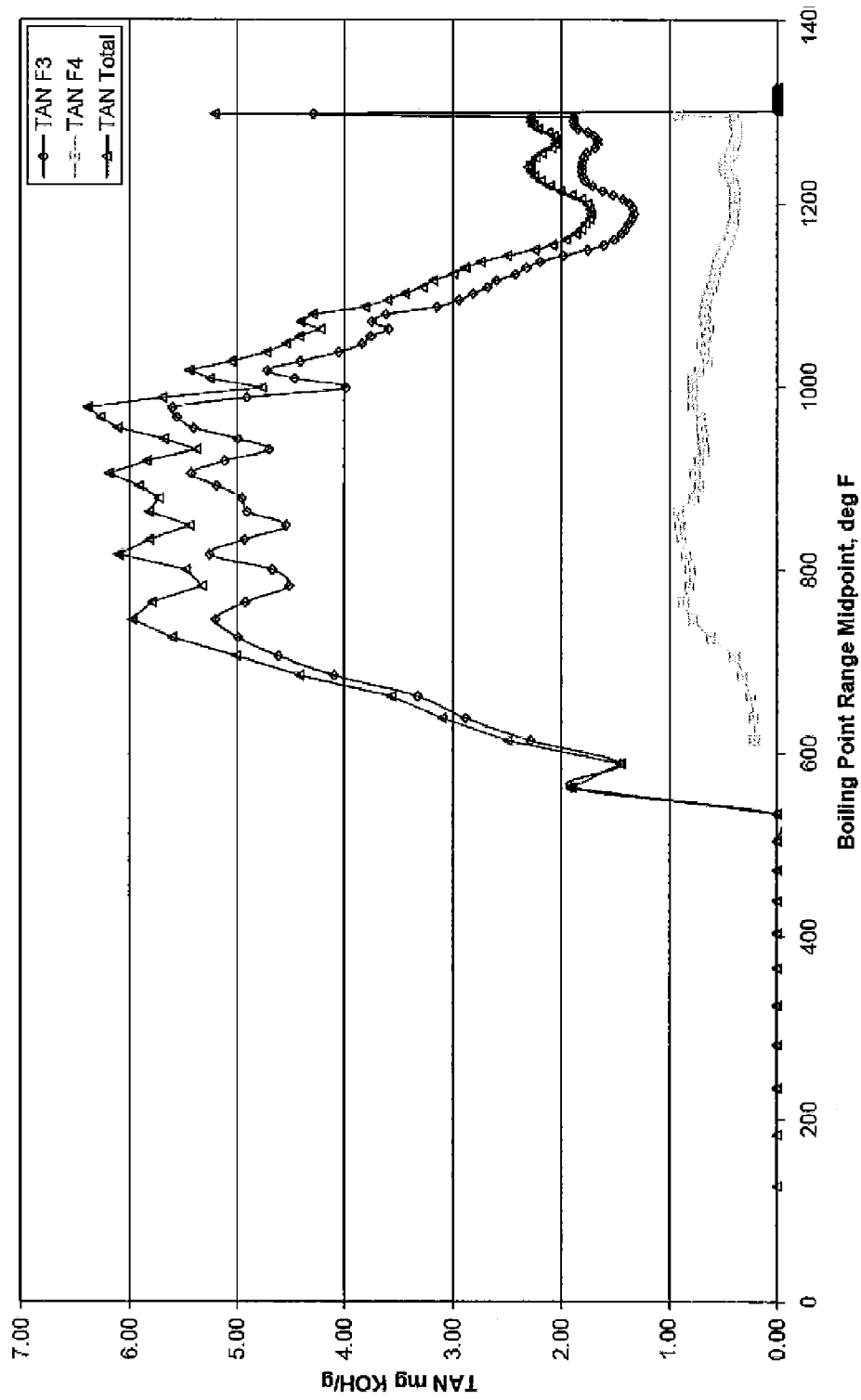
FIG. 14. SD results for Heidrun crude oil.
Figure 15:
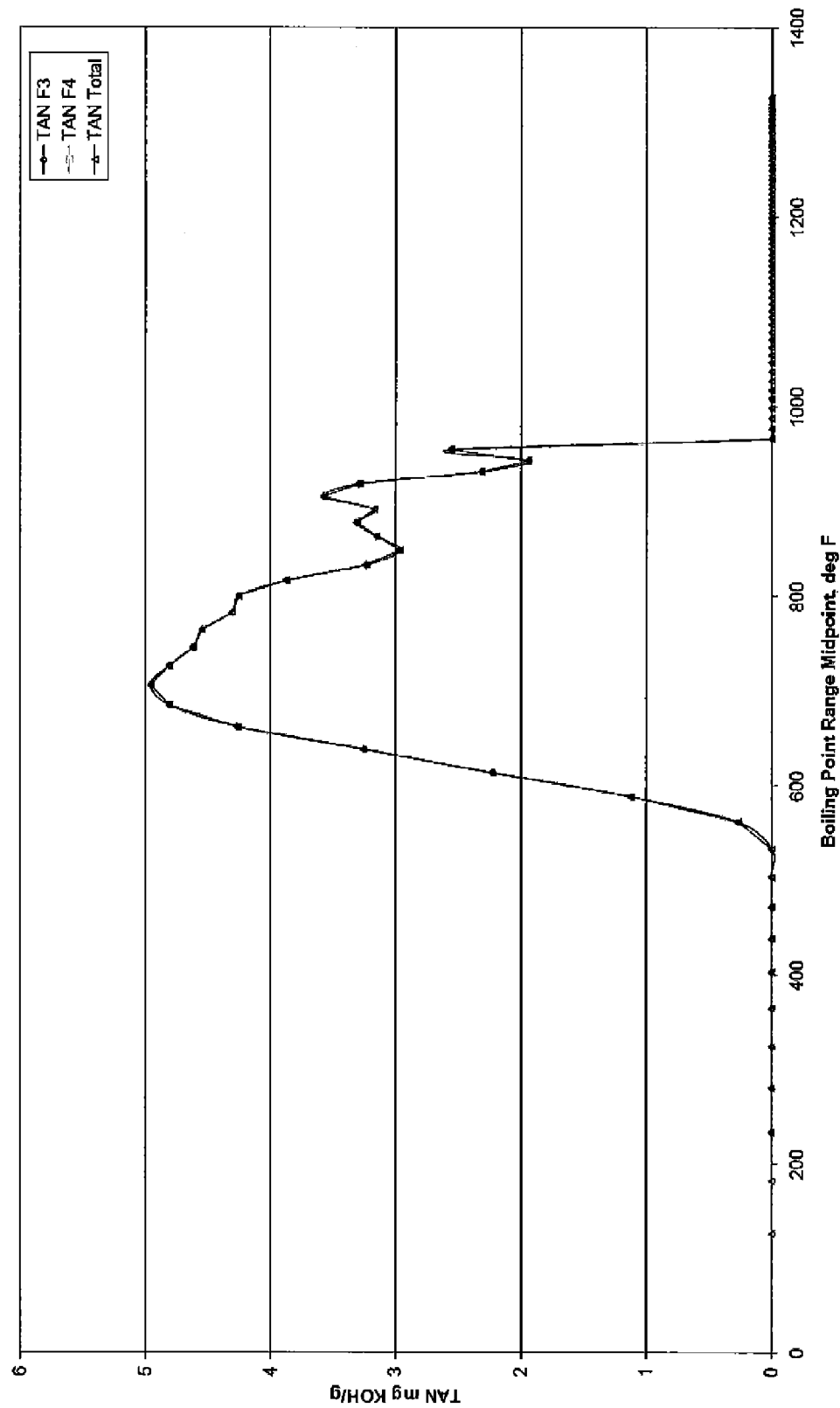
FIG. 15. SD results for Heidrun gas oil.
Figure 16:
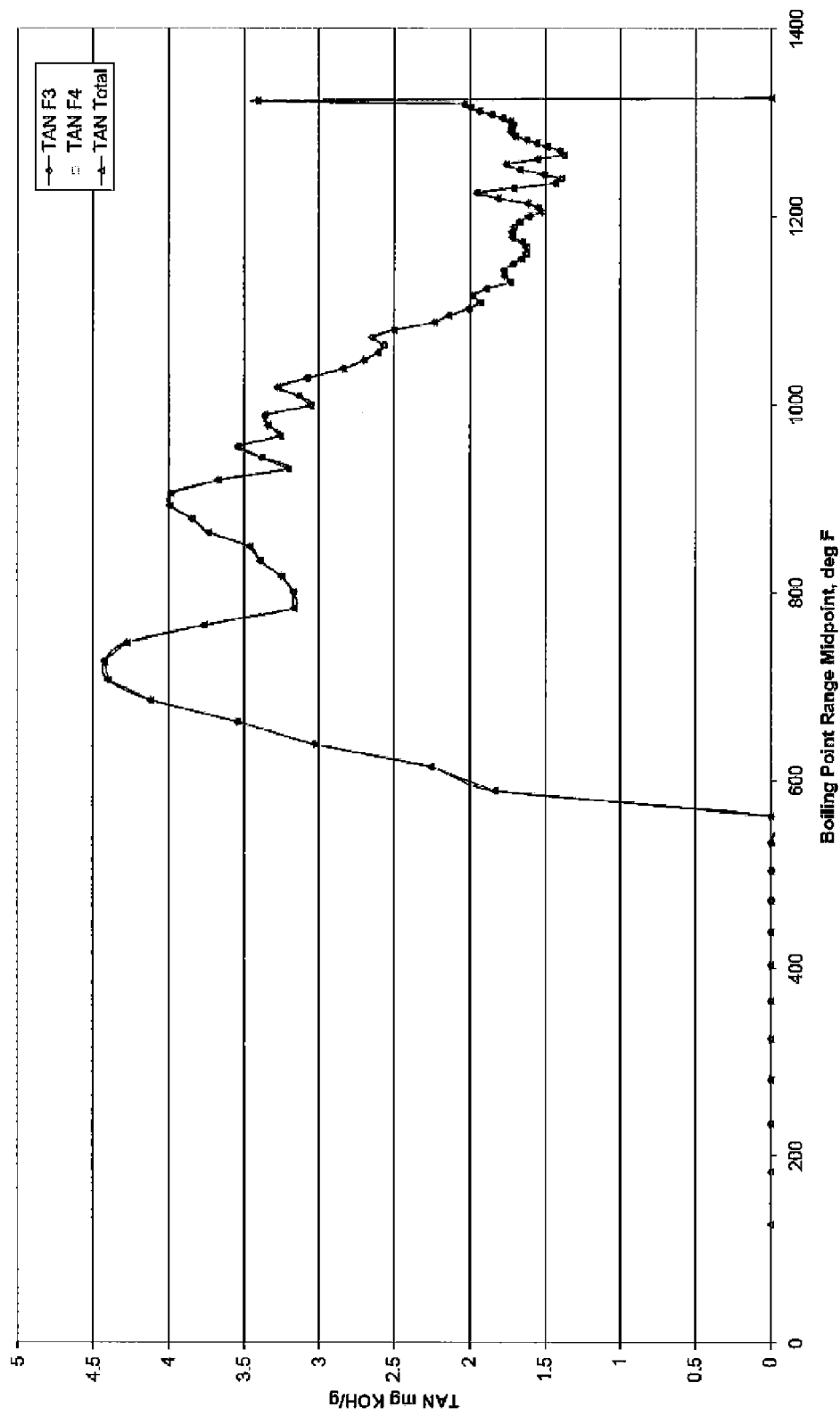
FIG. 16. SD results for San Joaquin Valley Heavy crude oil.
Figure 17:
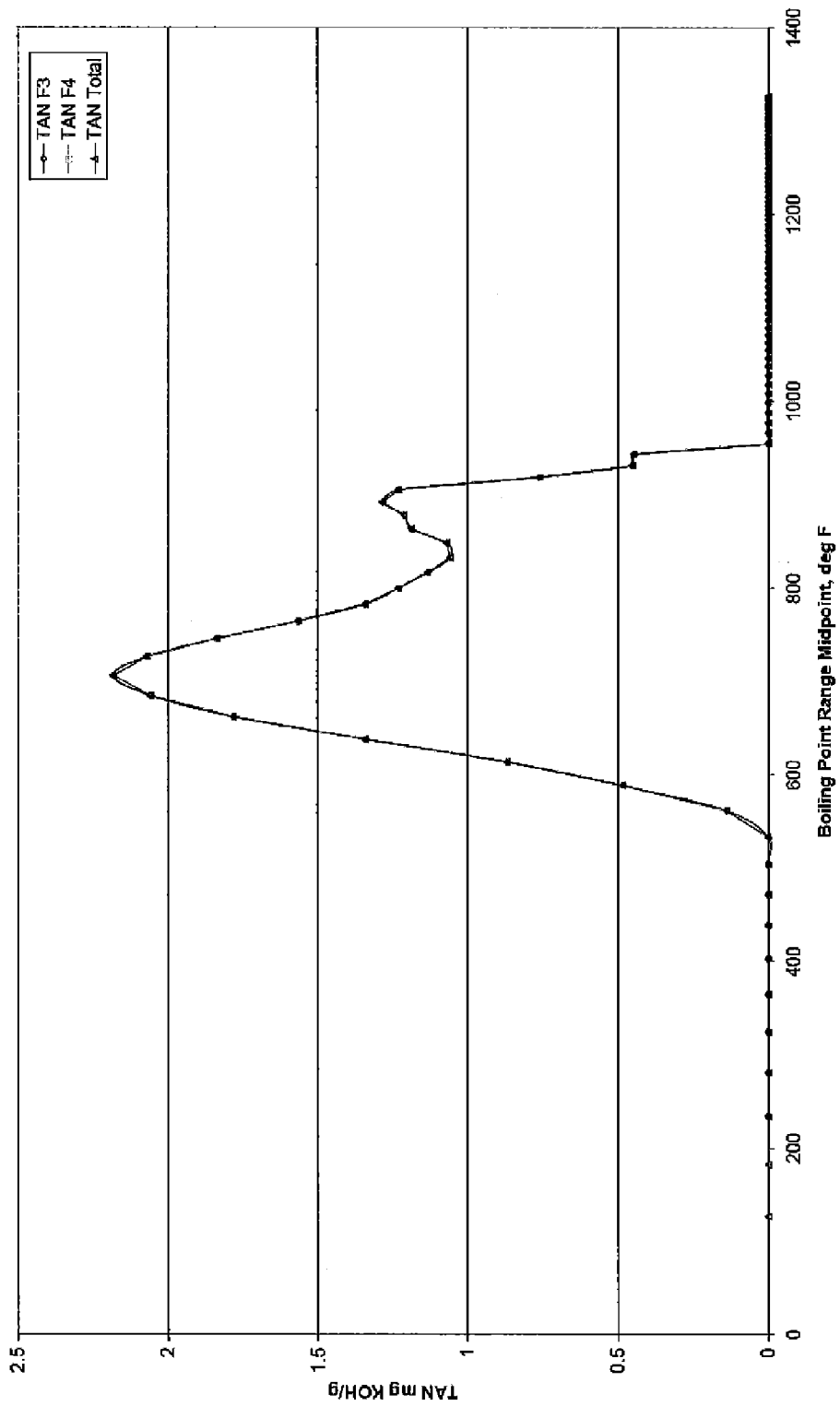
FIG. 17. SD results for San Joaquin Valley Heavy gas oil.

Data are presented from six crudes and their six gas oils: Petrozuata Bitumen (FIGS. 6 & 7), Bohai Bay (FIGS. 8 & 9), Doba (FIGS. 10 & 11), Grane (FIGS. 12 & 13), Heidrun (FIGS. 14 & 15), and San Joaquin Valley Heavy (FIGS. 16 & 17). These figures plotted the concentration of acid along the y-axis versus the distillation boiling point along the x-axis. Each graph contains lines for the total TAN at a given temperature along with the contributions of TAN made by carboxylic acids (F3) and multiacids (F4), when present. That is, the F4 fraction was not analyzed by SD when F4 was not present, so the cumulative TAN is equal to the F3 fraction. The TAN-SimDist data obtained from these studies is summarized in Table 7 below.

TABLE 7

Summary of TAN-SimDist data for Analyzed Crudes

| Crude Oil (Origin) | Heidrun (Norway) | San Joaquin Heavy (California) | Grane (Norway) | Doba (Chad) | Petrozuata Bitumen Heavy (Venezuela) | Bohai Bay (China) |
|---|---|---|---|---|---|---|
| TAN mg KOH/g | 3.02 | 2.53 | 2.20 | 4.79 | 3.51 | 3.00 |
| Sulfur, weight percent | 0.44 | 1.16 | 0.84 | 0.30 | 3.90 | 0.30 |
| API | 29.0 | 13.2 | 18.4 | 21.8 | 9.1 | 21.1 |
| SimDist 50% off Temp., ° F. | 650.7 | 885.3 | 803.7 | 928.3 | 1062.7 | 838.6 |
| FIG. showing data | 14 | 16 | 12 | 10 | 6 | 8 |

Figure 5:
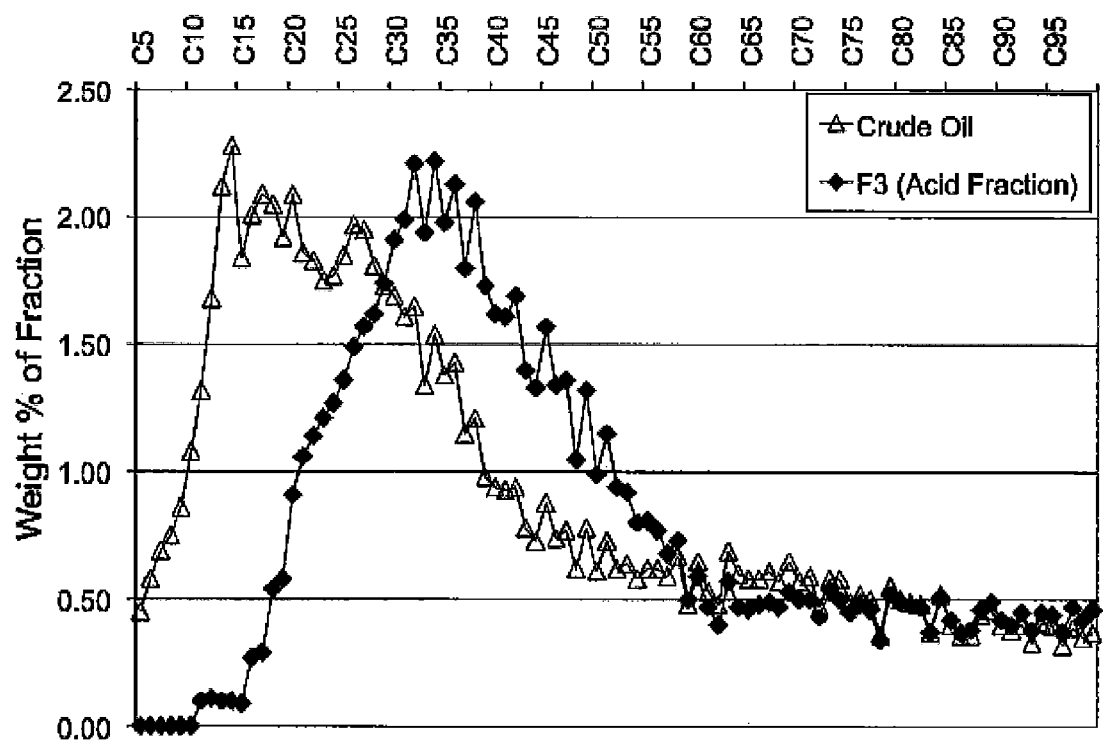
FIG. 5. SD results for Doba crude and its carboxylic acid-containing fraction obtained by liquid chromatographic separation. The data are plotted as a function of wt % of the fraction versus the ECN.
Figure 10:
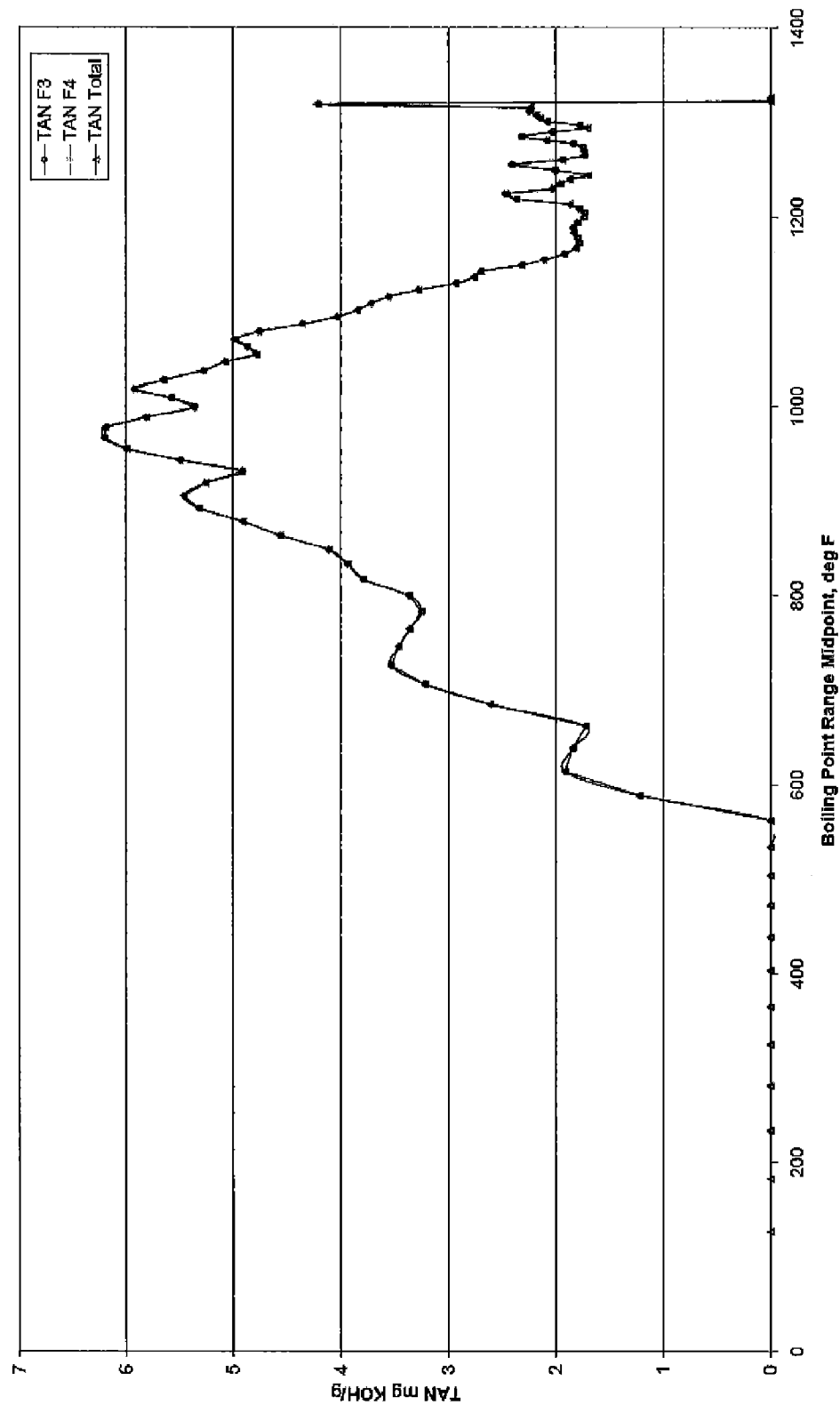
FIG. 10. SD results for Doha crude oil.

In particular, a double peak maximum in TAN values is visible in the Bohai Bay crude profile (FIG. 8), a level of detail not available by conventional methods. For Doba crude (FIG. 10), the TAN steadily rises from 600° F. (315° C.) until reaching a sample maximum near 975° F. (524° C.). Two or three local maxima exist from 600-1000° F. (315-538° C.) as the overall TAN increases. Above 1000° F., the calculated TAN decreases from 6 mg KOH/g to 2 mg KOH/mg at 1200° F. (649° C.). TAN values do not change as much between 1200° F. and the 1328° F. (720° C.) simulated distillation temperature limit. The last few chromatographic data points shown in FIG. 10 are the result of calculation sensitivities in the TAN calculations. Please note: The acid concentration profile in FIG. 10 is not the same as the weight percent distribution of acids in the crude as shown in FIG. 5.

The numerical values for weight percentages in each plot are internally relative for each sample and cannot be compared with each other. These plots allow the viewer to visualize the approximate weight percent distribution of the acid fractions in the hydrocarbon sample, including peak maxima and the character of the trailing edge. Results of this study can also be used to generate calculated distillation cuts and TAN values to study anomalous crude corrosion behavior.

Example 6

Comparison Between Tan Assay and Simulated Distillation Methods

The TAN values obtained from simulated distillation were compared to those obtained by conventional assay. TAN values obtained from SimDist varied from those obtained in a physical distillation. Some of the lower boiling distillates produced by physical distillation contained acids by virtue of minimum boiling azeotropes formed with aromatic hydrocarbons (e.g., toluene) and acetic acid, but SD predicts no low boiling acids (<365° F., <185° C.). Also, distillation towers produce imperfect separations with leading and trailing tails. Software, in contrast, mathematically produced perfect perpendicular separation at any temperature.

Figure 18:
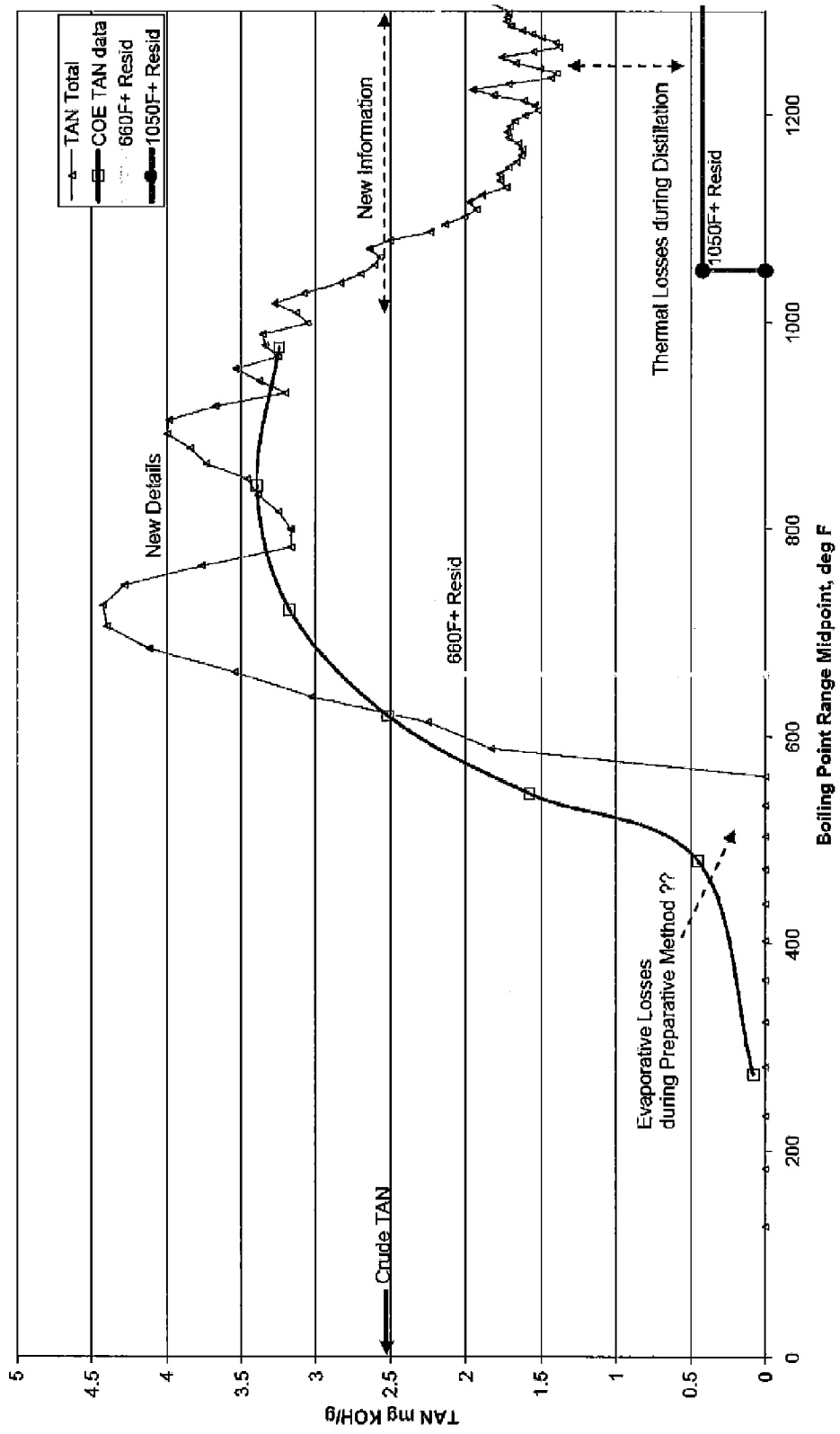
FIG. 18. Comparison of total acid number-simulated distillation (TAN SimDist) results with assay TAN data for San Joaquin Valley Heavy crude.
Figure 19:
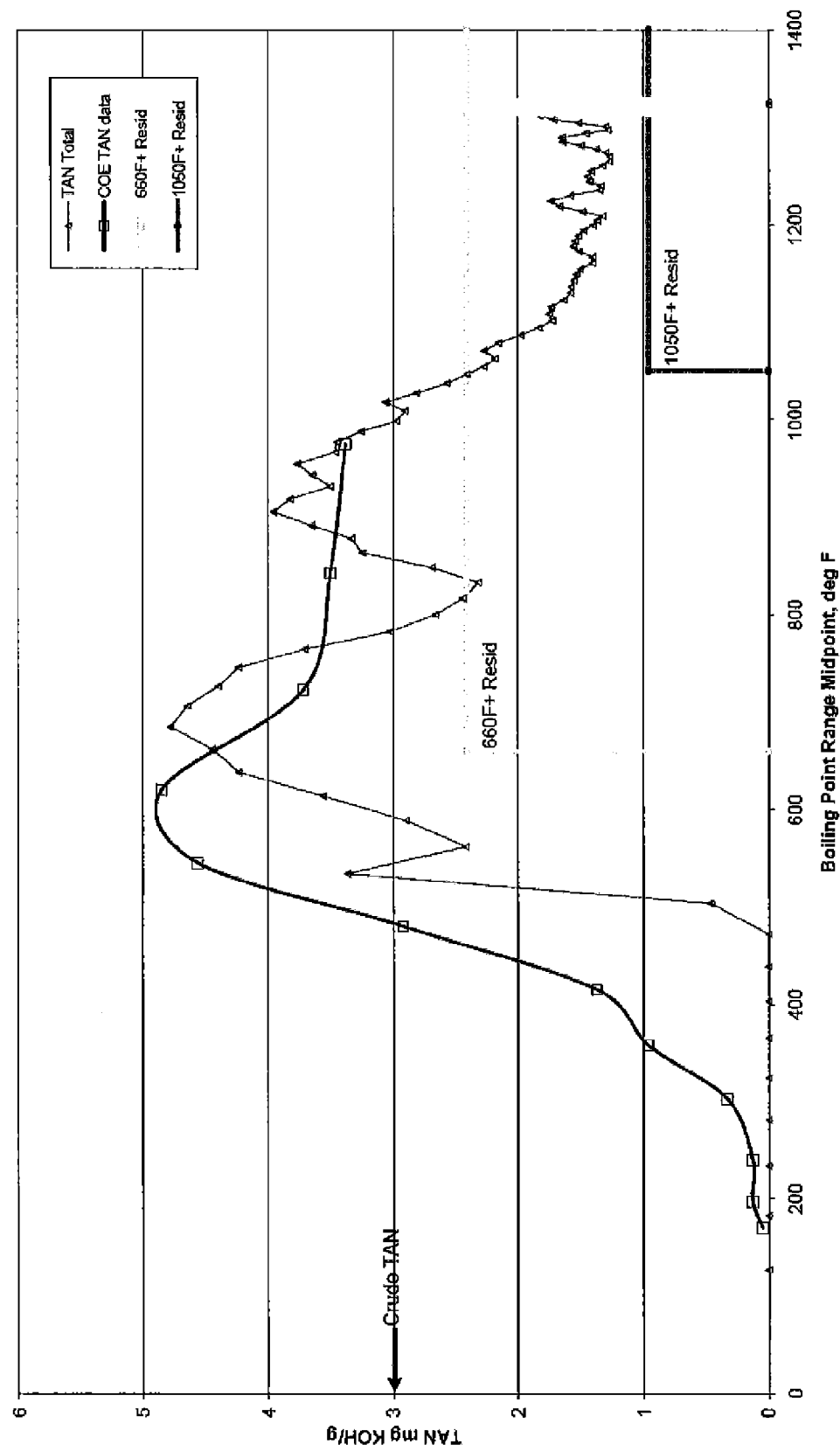
FIG. 19. Comparison of TAN SimDist results with assay TAN data for Bohai Bay crude.
Figure 20:
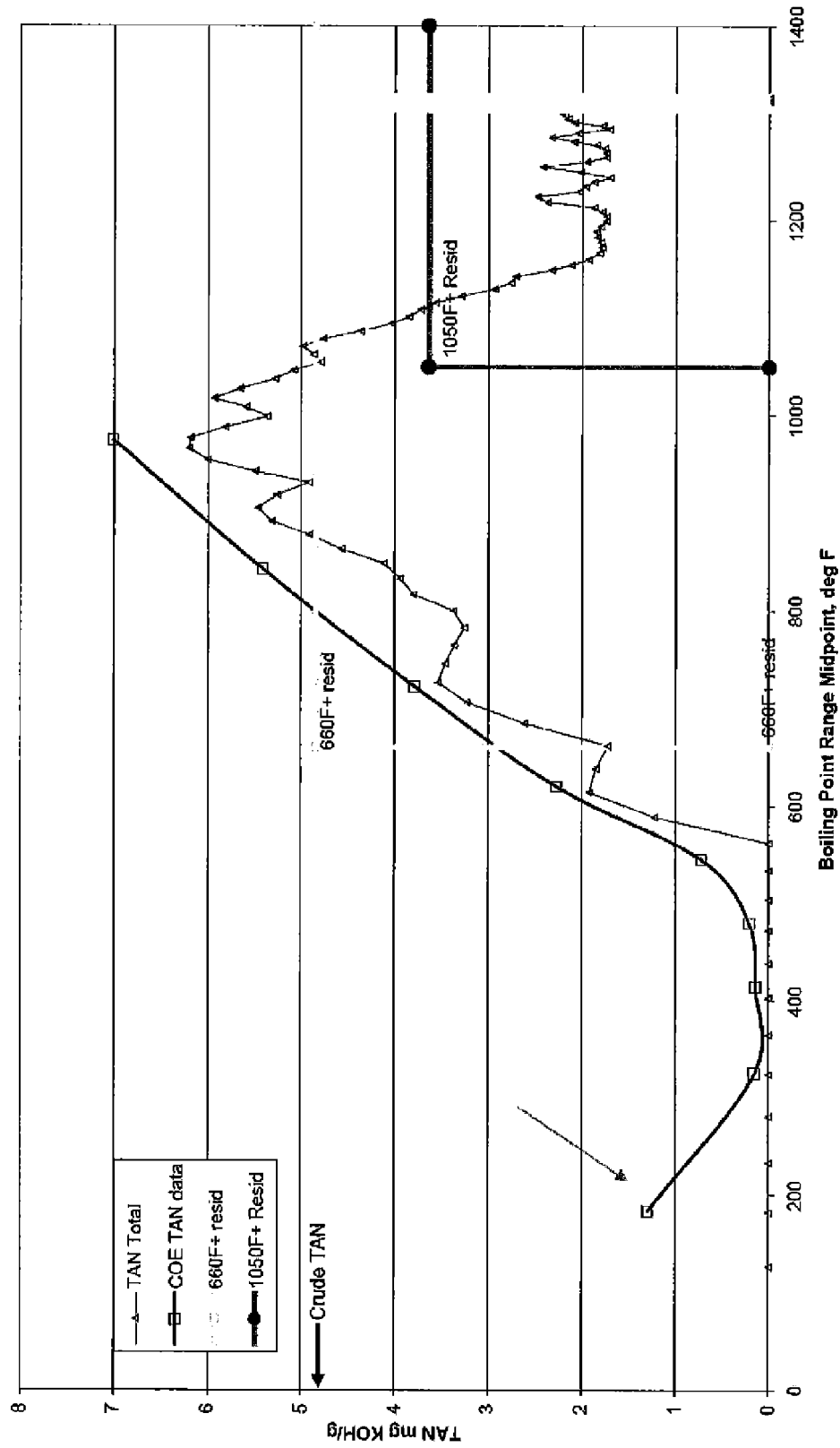
FIG. 20. Comparison of TAN SimDist results with assay TAN data for Doba crude.
Figure 21:
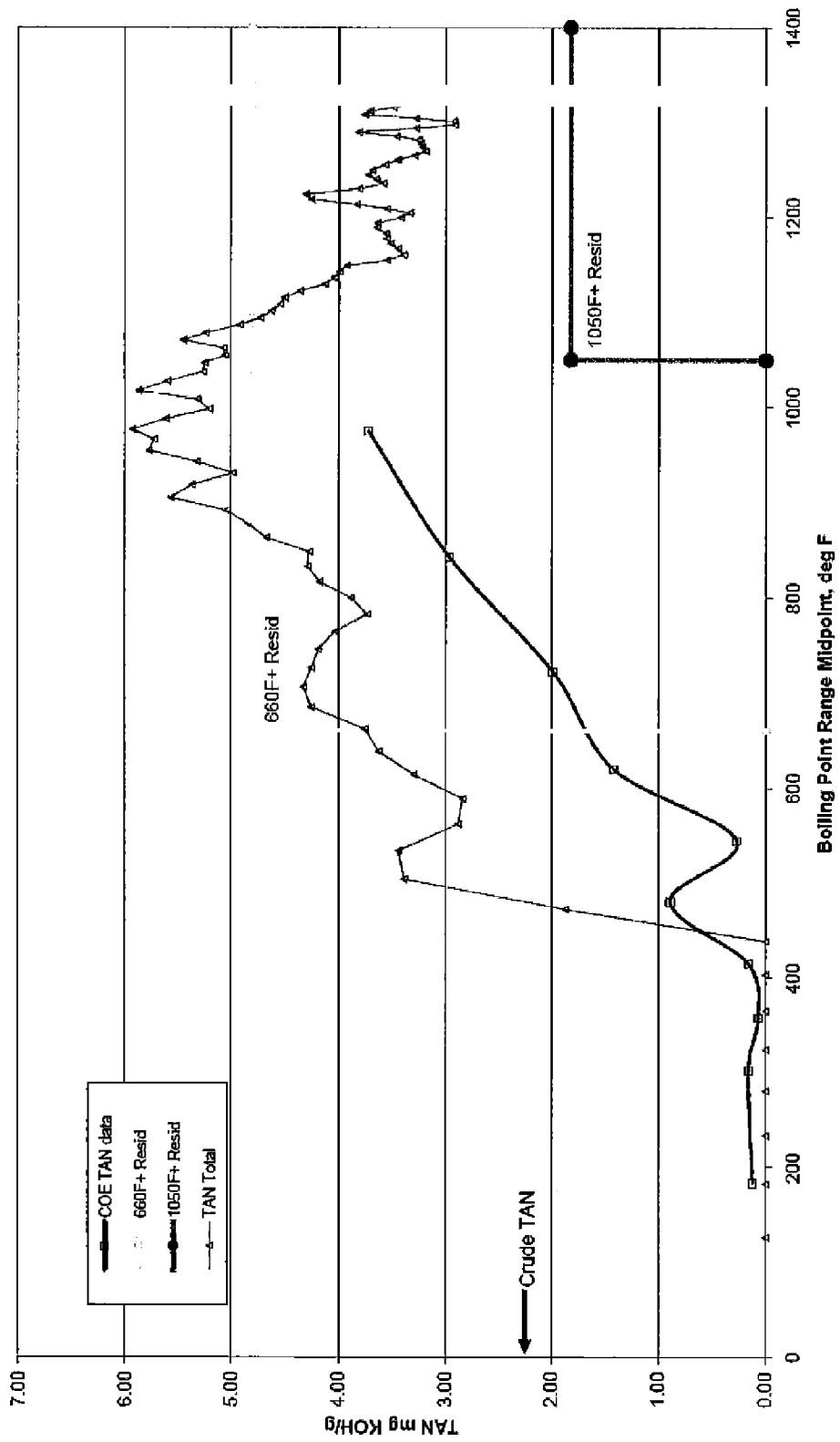
FIG. 21. Comparison of TAN SimDist results with assay TAN data for Grane crude.

Table 8 compares the TAN values measured by conventional assay with those calculated by the simulated distillation methods described herein. Details of this comparison can be seen in the plots overlaying the measured and calculated TAN data for San Joaquin Valley Heavy crude (FIG. 18), Bohai Bay crude (FIG. 19), Doba crude (FIG. 20), and Grane crude (FIG. 21).

TABLE 8

Comparison of Measured and Calculated TAN Values

| Crude Oil | Whole Crude | | 660° F.+ Residue | | | 1050° F.+ Residue | | |
|---|---|---|---|---|---|---|---|---|
| | Titration | TAN by SimDist Estimate | Titration | TAN by SimDist Balance | TAN by SimDist Estimate | Titration | TAN by SimDist Balance | TAN by SimDist Estimate |
| Bohai Bay | 3.0 | 2.3 | 2.41 | 3.7 | 2.6 | 0.96 | 4.0 | 1.6 |
| Doba | 4.8 | 2.7 | 4.85 | 6.1 | 3.1 | 3.64 | 7.7 | 2.4 |
| Grane | 2.2 | 3.6 | 4.80 | 2.2 | 4.3 | 1.82 | −1.5 | 3.8 |
| Heidrun | 3.0 | 2.6 | — | 5.4 | 4.5 | — | 5.3 | 2.4 |
| Petrozuata Bitumen | 3.5 | 4.3 | — | 3.7 | 4.6 | — | 2.2 | 3.6 |
| San Joaquin Valley Heavy | 2.5 | 2.5 | 2.18 | 2.9 | 2.9 | 0.42 | 2.0 | 1.8 |

For example, in the Bohai Bay crude oil sample (FIG. 19), at least one TAN unit was lost during actual distillation compared to SD. This was especially true in SD estimates TAN for vacuum gas oil (VGO) fractions, particularly for the residual where TAN was 1.83 by SD versus a TAN of 0.2 by actual distillation. In the light fractions, the calculated TAN is less than the actual TAN. This may be due to evaporative loss, or that some acids distill azotropically into the hydrocarbon fraction in actual distillation, but are not included in the SD.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The following references are incorporated by reference in their entirety:

"Designation D 7169-05: Standard Test Method for Boiling Point Distribution of Samples with Residues Such as Crude Oils and Atmospheric and Vacuum Residues by High Temperature Gas Chromatography", ASTM, 2005.

Qian et al., *Anal. Chem.*, 2008, 80(3): 849-855.

US20070037288.

U.S. Pat. No. 7,618,824.

US20020086434.

What is claimed:

1. A method for determining Total Acid Number (TAN) in a fluid fossil fuel, comprising:
   a. separating said fluid fossil fuel by liquid chromatography into a plurality of fractions, comprising at least one acidic fraction, and one polyacidic fraction;
   b. determining a boiling point distribution of said fluid fossil fuel by simulated distillation (SD);
   c. determining a boiling point distribution of said acidic fraction by simulated distillation (SD);
   d. determining a boiling point distribution of said polyacidic fraction by simulated distillation (SD);
   e. correlating said boiling point distribution of the fossil fuel with the boiling point distribution of the acidic fraction and with the polyacidic fraction along to determine acid molecular weights of the acidic fraction and the polyacidic fraction; and
   f. calculating the TAN of the fluid fossil fuel based on the acid molecular weights and boiling point distribution of the fluid fossil fuel, boiling point distribution of the acidic fraction and the boiling point distribution of the polyacidic fraction.

2. The method of claim 1, wherein said polyacidic faction comprises diacid, and said correlating step uses Equations 3 and 4

$$\Delta ECN_{Acid} = 4 + 2.2516 e^{-0.0838 CN} \quad \text{(Equation 3), and}$$

$$\Delta ECN_{Diacid} = 8 + 8.5671 e^{-0.0774 CN} \quad \text{(Equation 4),}$$

wherein ΔECN is the carbon number addition to the acid carbon number needed to have an n-paraffin with the same boiling point as the acid with carbon number CN.

3. The method of claim 2, where the correlating step further uses Equations 1 and 2:

$$\Delta T_{Acid} = 9.1(T/T_{100})^{-2.43} \quad \text{(Equation 1), and}$$

$$\Delta T_{Diacid} = 23.8(T/T_{100})^{-2.91} \quad \text{(Equation 2)}$$

wherein $\Delta T_{Acid}$ is the correction to apply in the correlation for each percentage of distillation fraction comprising an acid and $\Delta T_{Diacid}$ is the correction to apply in the correlation for each percentage of distillation fraction comprising a diacid.

4. The method of claim 1, wherein said fluid fossil fuel is a crude oil.

5. The method of claim 1, wherein said plurality of fractions comprises a first fraction, a second fraction, a third fraction, and a fourth fraction.

6. The method of claim 5, wherein said first fraction consists essentially of hydrocarbons, said second fraction consists essentially of weakly acidic compounds, said third fraction consists essentially of carboxylic acids, and said fourth fraction consists essentially of polyacids.

7. The method of claim 1, wherein said TAN has a resolution of at least 1 wt % and is calculated at each degree Fahrenheit.

8. The method of claim 1, wherein said method is automated.

9. The method of claim 1, wherein the steps of determining a boiling point distribution of the fossil fuel, determining a boiling point distribution of the acidic fraction and determining a boiling point distribution of the polyacidic fraction all utilize published standards for performing such simulated distributions including ASTM D 7096, ASTM D 7169 or an equivalent method.

10. The method of claim 1, wherein the liquid chromatography is HPLC using a 1-5×25-50 cm column packed with silica gel.

11. The method of claim 10, wherein in silica gel is 60 A silica gel.

12. The method of claim 10, wherein the column is eluted with a ternary solvent.

13. The method of claim 12, wherein the ternary solvent further comprises methanol and tetramethylammonium hydroxide (TMAH).

14. A method for determining Total Acid Number (TAN) in a fluid fossil fuel, comprising:

a. separating said fluid fossil fuel by high performance liquid chromatography (HPLC) into a first fraction consisting essentially of hydrocarbons, a second fraction consisting essentially of weakly acidic compounds, a third fraction consisting essentially of carboxylic acids, and a fourth fraction consisting essentially of polyacids comprising at least one diacid;

b. determining boiling point distribution of said fluid fossil fuel, of said third fraction, and of said fourth fraction by simulated distillation (SD);

c. correlating the boiling point distributions to acid molecular weight using Equations 1-4:

$$\Delta T_{Acid} = 9.1(T/T_{100})^{2.43} \quad \text{(Equation 1),}$$

$$\Delta T_{Diacid} = 23.8(T/T_{100})^{-2.91} \quad \text{(Equation 2),}$$

$$\Delta ECN_{Acid} = 4 + 2.2516 e^{-0.0838 CN} \quad \text{(Equation 3), and}$$

$$\Delta ECN_{Diacid} = 8 + 8.5671 e^{-0.0774 CN} \quad \text{(Equation 4),}$$

wherein ΔTacid and ΔTdiacid are corrections to be added to the reported n-paraffin boiling point to reflect the true boiling point of acids and diacids respectively; and wherein ΔECN is the carbon number addition to the acid carbon number needed to have an n-paraffin with the same boiling point as the acid with carbon number CN; and d. calculating TAN based on said acid molecular weights and the boiling point distributions of the fluid fossil fuel, the acidic fraction and the polyacidic fraction.

15. The method of claim 14, wherein said fluid fossil fuel is a crude oil.

16. The method of claim 14, wherein said TAN has a resolution of at least 1 wt % and is calculated at each degree Fahrenheit.

17. The method of claim 16, wherein said method is automated.

18. The method of claim 14, wherein said simulated distillation is performed at an atmospheric equivalent temperature of 720° C.

19. The method of claim 14, wherein SD uses the ASTM D 7096 or D 7169 method or an equivalent; and wherein the HPLC uses a 2.5×30 cm column packed with reverse phase 60-Å silica gel; and wherein the column is eluted with a ternary solvent comprising methanol with tetramethylammonium hydroxide (TMAH).

* * * * *